(12) United States Patent
Do

(10) Patent No.: US 9,566,316 B2
(45) Date of Patent: *Feb. 14, 2017

(54) VARIANT, RECOMBINANT BETA-GLUCOCEREBROSIDASE PROTEINS WITH INCREASED STABILITY AND INCREASED RETAINED CATALYTIC ACTIVITY

(71) Applicant: Amicus Therapeutics, Inc., Cranbury, NJ (US)

(72) Inventor: Hung V. Do, New Hope, PA (US)

(73) Assignee: AMICUS THERAPEUTICS, INC., Cranbury, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/987,204

(22) Filed: Jan. 4, 2016

(65) Prior Publication Data

US 2016/0184408 A1    Jun. 30, 2016

Related U.S. Application Data

(63) Continuation of application No. 14/611,495, filed on Feb. 2, 2015, now Pat. No. 9,254,313, which is a continuation of application No. 13/884,126, filed as application No. PCT/US2011/059731 on Nov. 8, 2011, now Pat. No. 8,962,564.

(60) Provisional application No. 61/411,331, filed on Nov. 8, 2010, provisional application No. 61/412,180, filed on Nov. 10, 2010.

(51) Int. Cl.
| | | |
|---|---|---|
| C07K 1/00 | (2006.01) | |
| C12N 9/24 | (2006.01) | |
| A61K 38/00 | (2006.01) | |
| A61K 38/47 | (2006.01) | |
| A61K 31/445 | (2006.01) | |

(52) U.S. Cl.
CPC ............. *A61K 38/47* (2013.01); *A61K 31/445* (2013.01); *C12N 9/2402* (2013.01); *C12Y 302/01045* (2013.01)

(58) Field of Classification Search
CPC .................. A61K 38/47; C12N 9/2402; C12Y 302/01045
USPC ........................................................ 435/183
See application file for complete search history.

(56) References Cited

U.S. PATENT DOCUMENTS

| | | | |
|---|---|---|---|
| 6,328,958 B1 | 12/2001 | Amalfitano et al. | |
| 6,524,613 B1 | 2/2003 | Steer et al. | |
| 8,487,110 B2 * | 7/2013 | Rybczynski et al. | C07D 211/46 546/242 |
| 2002/0127219 A1 | 9/2002 | Okkels et al. | |
| 2003/0215435 A1 | 11/2003 | Berent | |
| 2004/0009165 A1 | 1/2004 | Okkels et al. | |
| 2005/0265988 A1 | 12/2005 | Choi et al. | |
| 2007/0166813 A1 | 7/2007 | Futerman et al. | |
| 2009/0163368 A1 | 6/2009 | Liu et al. | |
| 2010/0041151 A1 | 2/2010 | Yew et al. | |

FOREIGN PATENT DOCUMENTS

| | | |
|---|---|---|
| CN | 1268186 | 9/2000 |
| CN | 1342206 | 3/2002 |
| CN | 101878303 | 11/2010 |
| WO | WO-90/07573 | 7/1990 |
| WO | WO-98/49350 | 11/1998 |
| WO | WO-99/40789 | 8/1999 |
| WO | WO 01/49830 | 7/2001 |
| WO | WO-2009/059056 | 5/2009 |
| WO | WO-2009/061369 | 5/2009 |

OTHER PUBLICATIONS

Extended European Search Report in EP11839428.7, dated Oct. 3, 2014, 14 pages.
Human glucocerebrosidase, GCB, mutant K321N, XP002720873, retrieved from EBI accession No. GSP/AAU05680, Oct. 2001, 1 page.
Human glucocerebrosidase, GCB, mutant K321N/T323S, XP002720874 retrieved from EBI accession No. GSP:AAU05681, Oct. 2011, 1 page.
Final Office Action in U.S. Appl. No. 13/884,126, dated Mar. 21, 2014, 8 pages.
Non-Final Office Action in U.S. Appl. No. 13/884,126, dated Oct. 18, 2013, 12 pages.
Non-Final Office Action in U.S. Appl. No. 13/884,126, dated Jul. 24, 2014, 8 pages.
Non-Final Office Action in U.S. Appl. No. 14/611,495, dated May 12, 2015, 6 pages.
PCT International Preliminary Report on Patentability Chapter II in PCT/US2011/059731, dated Feb. 7, 2013, 22 pages.
PCT International Search Report in PCT/US2011/059731, dated Jun. 1, 2012, 6 pages.

(Continued)

*Primary Examiner* — Maryam Monshipouri
(74) *Attorney, Agent, or Firm* — Servilla Whitney LLC

(57) ABSTRACT

Described herein are variant, recombinant β-glucocerebrosidase proteins characterized as having increased stability relative to recombinant wild-type β-glucocerebrosidase. Also provided herein are variant, recombinant β-glucocerebrosidase proteins characterized as retaining more catalytic activity relative to recombinant wild-type β-glucocerebrosidase. Further described herein are variant, recombinant β-glucocerebrosidase proteins that can have amino acid variations at one or more of the following positions: 316, 317, 321 and 145. Methods of making the variant, recombinant β-glucocerebrosidase proteins are also described as well as methods of treating patients having lysosomal storage diseases.

20 Claims, 3 Drawing Sheets

(56) References Cited

OTHER PUBLICATIONS

RecName: Full=Glucosylceramidase, UNIPROT:Q70KH2 XP-002720877 Jul. 5, 2004, 1 page.
RecName: Full=Glucosylcermidase, UNIPROT:QKHZ8 XP-002720876 Mar. 7, 2006, 1 page.
RecName: Full-Glucosylceramidase, UNIPROT:P17439 XP-002720875 Aug. 1, 1990, 2 pages.
Gao, Shu-Ying, et al., The Progress of Lysosome Thesaurosis, Apr. 12, 2004, 6 pages.
Grace, et al., Analysis of human acid beta-glucosidase by site-directed mutagenesis and heterologous expression, *J. Bio Chem.* 269(3) Jan. 21, 1994, 2283-91.
Liou, Benjamin, et al., Analyses of Varient Acid B-Glucosidases: Effects on Gaucher Disease Mutations, *J. Biol. Chem.* vol. 281 2006, 4242-4253.
Lopez-Camacho, et al., Amino acid substitutions enhancing thermostability of Bacillus polymyxa b-glucosidase A, *Biochem. J.* 3141996, 883-838.
Maegawa, et al., Identification and Characterization of Ambroxol as an Enzyme Enhancement Agent for Gaucher Disease, *The Journal of Biological Chemistry* 284 Aug. 28, 2009, 23502-23516.
O'Neill, Raymond R., et al., Comparison of the chromosomal localization of murine and human glucocerebrosidase genes and of the deduced amino acid sequences, *Proc. Natl. Acad. Sci. USA*, vol. 86 Jul. 1989, 5049-5053.
Smye, R., IPR80 Databse, Accession No. T18583, Oct. 1999, 1 page.
Steet, Richard, et al., Selective action of the iminosugar isofagomine, a pharmacological chaperone for mutant forms of acid-B-glucosidase, *Biochemical Pharmacology* 73 2007, 1376-1383.
Steet, Richard A., et al., The iminosugar isofagomine increases the activity of N370S mutant acid B-glucosidase in Gaucher fibroblasts by several mechanisms, *PNAS*, vol. 103, No. 37 XP-008129303 Sep. 12, 2006, 14813-13818.
Stratil, Antonin, et al., Comparative and genetic analysis of the procine glucocerebrosidase (GBA) gene, *Comparative Biochemistry and Physiology*, Part B 138 2004, 377-383.
Weinreb, Neal J., et al., Pharmacological Chaperone Therapy for the Treatment of Gaucher Disease: Results of Phase I Clinical Trials and a Clinical Ex Vivo Response Study with a Survey of Blood Markers for 53 Gaucher Patients, *Blood, American Society of Hematology*, vol. 110, No. 11, Part 1 XP-009130375 Nov. 1, 2007, 4 pages.
Wustman, BA, et al., Pharmacological Chaperone Therapy for the Treatment of Gaucher Disease: AT2101 Increases B-Glucocerebrosidase Levels in Cells, Mice and Healthy Human Volunteers, *J Inherit Metab Dis* 30, Suppl 1 XP-009124537 2007, 1 page.
Zhang, Yanli, et al., Cloning of human lysosomal acid B-glucosidase gene and its expression in COS7 cells, *Center of Animal Embryo Engineering and Technology* Nov. 13, 2008, 5 pages.

\* cited by examiner

VARIANT, RECOMBINANT BETA-GLUCOCEREBROSIDASE PROTEINS WITH INCREASED STABILITY AND INCREASED RETAINED CATALYTIC ACTIVITY

CROSS-REFERENCE TO RELATED APPLICATIONS

This application is a continuation under 35 U.S.C. §120 of U.S. patent application Ser. No. 14/611,495, filed Feb. 2, 2015, which is a continuation of U.S. patent application Ser. No. 13/884,126, filed Nov. 8, 2011, now issued as U.S. Pat. No. 8,962,564, which is the National Phase entry of PCT/US11/59731, filed Nov. 8, 2011, which claims priority under 35 U.S.C. §119(e) to provisional U.S. Provisional Application Ser. No. 61/411,331, filed Nov. 8, 2010, and U.S. Provisional Application Ser. No. 61/412,180, filed Nov. 10, 2010, all of which are incorporated herein by reference and in their entireties.

TECHNICAL FIELD

The field of this invention includes proteins that are useful in enzyme replacement therapy for various lysosomal storage diseases. These lysosomal storage diseases include Gaucher disease.

BACKGROUND

β-glucocerebrosidase is a soluble lysosomal enzyme that functions at the luminal membrane surface through interactions with Saposin C and anionic phospholipids to hydrolyze the glycolipid glucosylceramide. β-glucocerebrosidase is particularly important in tissue macrophages to break down and recycle membranes from engulfed damaged cells and pathogens. Since glucosylceramide is the primary precursor molecule for more than 300 glycolipids and gangliosides that are involved in numerous important cellular pathways and signaling cascades, it is essential to maintain the intricate balance for these various lipid molecules.

Gaucher disease is caused by a deficiency in β-glucocerebrosidase that results in the accumulation of glucosylceramide. Gaucher disease manifests itself through various clinical symptoms including anemia, thrombocytopenia, hepatosplenomegaly and skeletal abnormalities. Gaucher disease is classified in three categories based on neurological involvement: type 1 (non-neuronopathic); type 2 (acute neuronopathic); and type 3 (chronic neuronopathic). There is no known cure for Gaucher disease, but enzyme replacement therapy (ERT), which supplements the deficient β-glucocerebrosidase and substrate reduction therapy which inhibits the synthesis of glucosylceramide are approved treatments for this disease. Other therapeutic approaches such as small molecule pharmacological chaperones and protein folding modulators are also being evaluated as potential treatments of this disease. Of these treatment approaches, ERT is the most established and effective clinical treatment for the visceral symptoms of Gaucher disease. Imiglucerase (recombinant β-glucocerebrosidase; Cerezyme™, Genzyme Corp.™) was developed and approved by the FDA in 1994 for the treatment of Gaucher disease and is currently the standard of care for this disease.

While Cerezyme™ ERT is widely considered to be the most effective treatment, this lysosomal enzyme is not stable at neutral pH and 37° C. In fact, the vast majority of the drug is irreversibly inactivated in blood shortly after intravenous infusion. Only the small fraction that retains catalytic activity and is internalized into the target macrophages confers the entire therapeutic effect. Hence, it would be advantageous to develop a more stable β-glucocerebrosidase enzyme that is not as susceptible to enzyme inactivation from the protein production step through physiological conditions that would be encountered upon introduction into a human subject in need thereof.

SUMMARY

Provided herein are variant, recombinant β-glucocerebrosidase proteins characterized as having increased stability relative to wild-type, recombinant β-glucocerebrosidase. Also provided herein are variant, recombinant β-glucocerebrosidase proteins characterized as retaining more catalytic activity relative to wild-type, recombinant β-glucocerebrosidase. Further described herein are variant, recombinant β-glucocerebrosidase proteins that can have amino acid variations at one or more of the following positions: 316, 317, 321 and 145.

Described herein are methods of making the variant, recombinant β-glucocerebrosidase proteins characterized as retaining more catalytic activity relative to wild-type, recombinant β-glucocerebrosidase. Further described herein are compositions comprising the variant, recombinant β-glucocerebrosidase proteins and a pharmaceutically acceptable carrier. Also provided herein are compositions comprising the variant, recombinant β-glucocerebrosidase proteins and a pharmaceutically acceptable buffer.

Described herein are variant, recombinant β-glucocerebrosidase proteins having one or more replacement amino acids in the loop1 region of the protein, the one or more replacement amino acids characterized as having a side-chain conformation that increases order near the active site of the protein. Further described herein are variant, recombinant β-glucocerebrosidase proteins having one or more replacement amino acids in an α-helix near the active site (α6) of the protein, the one or more replacement amino acid side-chain characterized as having a side-chain confirmation that stabilizes this helix and pulls adjacent loop1 away from the catalytic site and has an open and active conformation. Also provided herein are variant, recombinant β-glucocerebrosidase proteins having one or more replacement amino acids in the random coil region between beta-sheet (β2) and an α-helix (α2), the one or more replacement amino acid side-chains characterized as having a side-chain confirmation that facilitates better interactions between different residues and secondary structures for improved stability.

Provided herein are methods for treating a lysosomal storage disease by administering to a subject in need thereof a variant, recombinant β-glucocerebrosidase protein characterized as having increased stability compared to wild-type, recombinant β-glucocerebrosidase. Also provided herein are methods for treating a lysosomal storage disease by administering to a subject in need thereof a variant, recombinant β-glucocerebrosidase protein characterized as retaining increased catalytic activity compared to wild-type, recombinant β-glucocerebrosidase. Also provided herein are methods for treating a lysosomal storage disease by administering to a subject in need thereof a variant, recombinant β-glucocerebrosidase protein characterized as having an increased specific activity compared to wild-type, recombinant β-glucocerebrosidase. Also provided herein are methods for treating a lysosomal storage disease by administering to a subject in need thereof a variant, recombinant β-glucocerebrosidase protein having an amino acid variation at one or more of the following positions: 316, 317, 321, and 145. Also provided herein are methods for treating Gaucher disease by administering to a subject in need thereof a variant, recombinant β-glucocerebrosidase protein.

Also provided herein are compounds comprising a variant, recombinant β-glucocerebrosidase protein characterized as having any one of the following amino acid sequences: SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, or SEQ ID NO: 16.

Also provided herein are variant, recombinant β-glucocerebrosidase proteins characterized as capable of increased expression relative to wild-type, recombinant β-glucocerebrosidase.

Also provided herein are methods of making a compound comprising a variant, recombinant β-glucocerebrosidase protein characterized as having any one of the following amino acid sequences: SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, or SEQ ID NO: 16. Also provided herein are methods of making a nucleic acid encoding a variant, recombinant β-glucocerebrosidase protein characterized as having any one of the following amino acid sequences: SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, or SEQ ID NO: 16.

BRIEF DESCRIPTION OF THE DRAWINGS

The foregoing and other aspects of the present invention is apparent from the following detailed description of the invention when considered in conjunction with the accompanying drawings. For the purpose of illustrating the invention, there is shown in the drawings embodiments that are presently preferred, it being understood, however, that the invention is not limited to the specific instrumentalities disclosed. The drawings are not necessarily drawn to scale. In the drawings.

DETAILED DESCRIPTION OF ILLUSTRATIVE EMBODIMENTS

Figure 1:
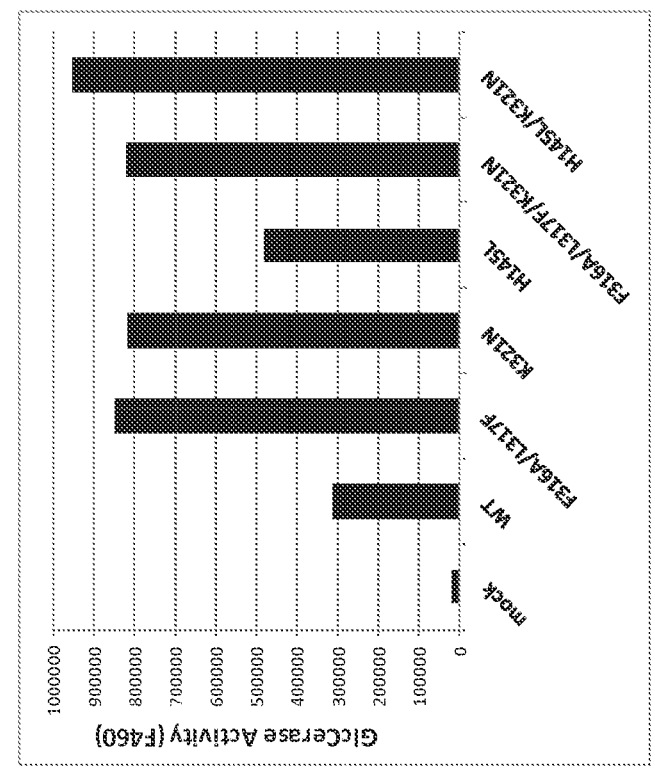
FIG. 1(A) shows enzyme activity measurements to compare the relative expression of variant, recombinant β-glucocerebrosidase proteins to the wild-type enzyme secreted into cell culture medium from a typical transient transfection experiment after 48 hrs; (B) shows a western blot analysis to compare the relative amounts of secreted variant, recombinant β-glucocerebrosidase proteins and the wild-type GlcCerase protein in cell culture medium after transient transfection.
Figure 1:
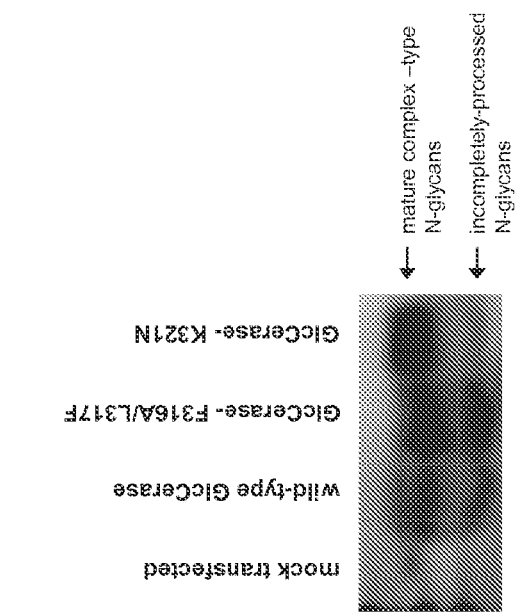

The present subject matter may be understood more readily by reference to the following detailed description taken in connection with the accompanying figures and examples, which form a part of this disclosure. It is to be understood that this invention is not limited to the specific devices, methods, applications, conditions or parameters described and/or shown herein, and that the terminology used herein is for the purpose of describing particular embodiments by way of example only and is not intended to be limiting of the claimed invention.

Also, as used in the specification including the appended claims, the singular forms "a," "an," and "the" include the plural, and reference to a particular numerical value includes at least that particular value, unless the context clearly dictates otherwise. The term "plurality", as used herein, means more than one. When a range of values is expressed, another embodiment includes from the one particular value and/or to the other particular value. Similarly, when values are expressed as approximations, by use of the antecedent "about," it is understood that the particular value forms another embodiment. All ranges are inclusive and combinable.

Examples are provided to assist in a further understanding of the inventions. Particular materials used, protocols and conditions are intended to be further illustrative of the inventions and should not be construed to limit the reasonable scope thereof.

Unless noted differently, variant, recombinant β-glucocerebrosidase protein properties are stated relative to wild-type, recombinant β-glucocerebrosidase protein properties (SEQ ID NO: 1). Herein, "GlcCerase" is an abbreviation used for β-glucocerebrosidase. All amino acid numbers are relative to SEQ. ID. NO. 1. Thus, position 145 would be the 145th amino acid occurring in SEQ. ID. NO. 1. Furthermore, variant, recombinant β-glucocerebrosidase proteins as disclosed herein also include functional fragments or derivatives thereof.

Herein, "about neutral pH" is meant to include the pHs that are normally considered physiological pHs (i.e., a pH of about 7.5 at 37° C.).

Suitable variant, recombinant β-glucocerebrosidase proteins can be characterized as having similar or increased protein expression and secretion into cell culture medium relative to wild-type, recombinant β-glucocerebrosidase proteins during cell culture and protein production. Suitable variant, recombinant β-glucocerebrosidase proteins can be characterized as having increased stability relative to wild-type, recombinant β-glucocerebrosidase proteins. These proteins have increased stability at physiological conditions and those physiological conditions can be in vivo. Further, these proteins can also be characterized as having increased stability at conditions of about neutral pH and about 37° C. This increased stability can be monitored at conditions of about neutral pH and about 37° C. over a period of about three hours. The increased stability is retained in cell culture medium and can be retained inside cells. These proteins can also have increased stability inside the lysosome and inside the lysosome the conditions can be about pH 5 and about 37° C. These proteins can also have increased stability that is characterized by reduced proteolytic degradation and the reduced proteolytic degradation can occur in cells. Further, the reduced proteolytic degradation can be in the lysosome in the cells. These proteins can also have increased stability at non-physiological conditions such as in buffer solutions during protein purification. These buffer solutions can have a pH greater than about 7 or a pH less than about 3 during protein purification. These buffer solutions can also contain organic solvents or chaotropic salts. These proteins can also have increased stability in buffer solutions at temperatures that range from about 2° C. to about 37° C. Further, these proteins can also have increased stability in buffer solutions at temperatures that range from about 2° C. to about 8° C. Also, these proteins can have increased stability in buffer solutions at a temperature about 20° C. These proteins can also have increased stability after freeze-thaw cycles or reconstitution after lyophilization. These proteins can also have increased stability in a drug-formulation buffer such as saline.

Suitable variant, recombinant β-glucocerebrosidase proteins, can be characterized as retaining more catalytic activity relative to wild-type, recombinant β-glucocerebrosidase. These proteins have retained more catalytic activity at physiological conditions and the more retained catalytic activity can be in vivo. Further, these proteins can also be characterized as having retained more catalytic activity at conditions of about neutral pH and about 37° C. This more retained catalytic activity can be monitored at conditions of about neutral pH and about 37° C. over a period of about two hours. These proteins have retained more catalytic activity in cell culture medium and the more retained catalytic activity can be inside cells. Further, these proteins can have retained more catalytic activity inside the lysosome and inside the lysosome the conditions can be about pH 5 and about 37° C. These proteins can also have retained more catalytic activity that is characterized by reduced proteolytic degradation and the reduced proteolytic degradation can occur in cells. Further, the reduced proteolytic degradation can be in the lysosome in the cells. These proteins can also have retained more catalytic activity at non-physiological conditions such as in buffer solutions during protein purification. These buffer solutions can have a pH greater than about 7 or a pH less than about 3 during protein purification. These buffer solutions can also contain organic solvents or chaotropic salts. These proteins can also have retained more catalytic activity at temperatures that range from about 2° C. to about 37° C. Further, these proteins can also have retained more catalytic activity at temperatures that range from about 2° C. to about 8° C. Also, these proteins can have retained more catalytic activity at a temperature of about 20° C. These proteins can also have retained more catalytic activity after freeze-thaw cycles or reconstitution after lyophilization. These proteins can also have retained more catalytic activity in a drug-formulation buffer such as saline.

Variant, recombinant β-glucocerebrosidase proteins can also have an amino acid variation at one or more of the following positions: 316, 317, 321 and 145. These proteins can have the amino acid variation or variations: (1) F316A and L317F; or (2) K321N; or (3) H145L; or (4) H145F; or (5) F316A, L317F, and K321N; or (6) K321A; or (7) K321V; (8) F316A, L317F, and K321A; or (9) F316A, L317F, and K321V; or (10) H145L, F316A, and L317F; or (11) H145L and K321N; or (12) H145L and K321A; or (13) H145L and K321V. Some of these proteins can also be characterized as having similar or increased protein expression and secretion into cell culture medium relative to wild-type, recombinant β-glucocerebrosidase proteins during cell culture and protein production. These proteins can also be characterized as having increased stability relative to wild-type, recombinant β-glucocerebrosidase. These proteins can also be characterized as having increased stability at physiological conditions and these conditions are about neutral pH and about 37° C. These proteins can also be characterized as retaining more catalytic activity relative to wild-type, recombinant β-glucocerebrosidase. The catalytic activity can be measured after incubation at conditions of about neutral pH and about 37° C. over a period of about two hours. These proteins can also be characterized as retaining more catalytic activity at physiological conditions. The variant, recombinant β-glucocerebrosidase protein with the amino acid variations F316A and L317F has an extended apparent half-life of at least about 2-fold longer than wild-type, recombinant β-glucocerebrosidase. The variant, recombinant β-glucocerebrosidase protein with the amino acid variation K321N has an extended apparent half-life of at least about 3-fold longer than wild-type, recombinant β-glucocerebrosidase. The variant, recombinant β-glucocerebrosidase protein with the amino acid variation K321A has an extended apparent half-life of at least about 3-fold longer than wild-type, recombinant β-glucocerebrosidase. The variant, recombinant β-glucocerebrosidase protein with the amino acid variation K321V has an extended apparent half-life of at least about 1.4-fold longer than wild-type, recombinant β-glucocerebrosidase. The variant, recombinant β-glucocerebrosidase protein with the amino acid variation H145L has an extended apparent half-life of at least about 3-fold longer than wild-type, recombinant β-glucocerebrosidase. The variant, recombinant β-glucocerebrosidase protein with the amino acid variation H145F has an extended apparent half-life of at least about 2-fold longer than wild-type, recombinant β-glucocerebrosidase. The variant, recombinant β-glucocerebrosidase protein with the amino acid variations F316A, L317F, and K321N has an extended apparent half-life of at least about 3-fold longer than wild-type, recombinant β-glucocerebrosidase. The variant, recombinant β-glucocerebrosidase protein with the amino acid variations H145L, F316A, and L317F has an extended apparent half-life of at least about 2-fold longer than wild-type, recombinant β-glucocerebrosidase. The variant, recombinant β-glucocerebrosidase protein with the amino acid variations H145L and K321N has an extended apparent half-life of at least about 3-fold longer than wild-type, recombinant β-glucocerebrosidase. This extended apparent half-life can be measured after incubation at conditions of about neutral pH and about 37° C. over a period of about two hours.

Example 1

Reagents 4-methylumbelliferyl-β-D-glucoside (4MUG) fluorogenic substrate was purchased from Research Products International (Mt. Prospect, Ill.). DNA Gel Extraction and Miniprep DNA® kits were from QIAGEN® (Valencia, Calif.). PureYield Maxiprep DNA Kit™ was from Promega™ (Madison, Wis.). Unless stated otherwise, chemicals were from Sigma™ (St. Louis, Mo.). Fugene-HD™ transfection reagent was from Roche™ (Indianapolis, Ind.). pEF6/V5-HisA™ mammalian expression vector, Dulbecco's modified Eagle medium (DMEM), fetal bovine serum (FBS) and other tissue culture reagents were from Invitrogen™ (Carlsbad, Calif.). Wild-type human wild-type β-glucocerebrosidase cDNA (NM 000157.3) was purchased from Origene™ (Rockville, Md.). Restriction endonucleases, Phusion-HF™ DNA polymerase, T4 DNA ligase, Antarctic phosphatase, chemically-competent E. coli (DH5β cells) and endoglycosidases PNGaseF and EndoH were all purchased from New England Biolabs™ (Ipswich, Mass.). Human embryonic kidney cells (transformed with the T-antigen; HEK293T) was from ATCC™.

Assays

Variant, recombinant β-glucocerebrosidase proteins and wild-type, recombinant β-glucocerebrosidase protein were all tested by transient expression in a human cell line (HEK293T) to assess protein expression. The reporter system to test catalytic activity of the variant, recombinant β-glucocerebrosidase proteins or wild-type, recombinant β-glucocerebrosidase protein was the ability to hydrolyze the 4-MU-β-glucose fluorogenic substrate at about pH 5.2 and about 37° C. The stability of these variant, recombinant β-glucocerebrosidase proteins and the purified wild-type, recombinant β-glucocerebrosidase protein was tested by monitoring of the retention of catalytic activity of each protein after incubation at about neutral pH and about 37° C. over a period of about 3 hours. The conditions in these experiments were designed to resemble the environment that would exist during the intravenous infusion of β-glucocerebrosidase protein enzyme replacement therapy into a patient.

More specifically but in no way to be construed as limiting, HEK293T cells were plated in 12-well tissue culture plates with 1 ml of DMEM medium supplemented with 10% FBS and incubated at 37° C. with a 5% $CO_2$ atmosphere. When the HEK293T cells reached 80-90% confluency, the spent medium was replaced with 1 ml of fresh DMEM/10% FBS medium and each well was transfected with 1 μg plasmid DNA for individual β-glucocerebrosidase proteins or PBS (for a mock-transfected negative control) and 3 μl of Fugene-HD transfection reagent according to the manufacturer's protocol. Transfected cells were incubated for 24-72 hours and checked daily for expression of recombinant β-glucocerebrosidase protein (secreted into medium) via enzyme activity assays.

β-glucocerebrosidase protein expression (and secretion into cell culture medium) was assessed by enzyme activity assays using conditioned medium from transient transfection experiments after 24, 48 or 72-hrs and the 4-methyl-umbelliferyl-β-D-glucoside (4-MUG) fluorogenic substrate. Briefly, 20 μl of conditioned media from each sample was harvested at the indicated time points and diluted with 80 μl McIlvane buffer (MI buffer: 50 mM sodium citrate/sodium phosphate (pH 5.2)/0.25% (v/v) Triton X-100/0.25% (w/v) sodium taurocholate) in 0.5 ml microcentrifuge tubes. Twenty five μl of each diluted sample was aliquotted into individual wells of 96-well black clear bottom plates (performed in triplicate) and 50 μl of 6 mM 4-MUG substrate (prepared in MI buffer) was added to each well via a multi-channel pipettor. The plates were then sealed with cover tape and incubated at 37° C. for 1 hr. The enzymatic reactions were halted by adding 125 μl of 0.1 M NaOH and the liberated 4-MU fluorescence was read on a fluorescence plate reader using 355 nm excitation and 460 nm emission wavelengths, respectively. The 4-MU fluorescence from the mock-transfected sample served as the "background" control and subtracted from all β-glucocerebrosidase protein samples.

To estimate the amount of wild-type and variant acid β-glucocerebrosidase proteins present in cell culture medium, conditioned cell culture media from transient transfection experiments were subjected to sodium dodecylsulfate polyacrylamide gel electrophoresis (SDS-PAGE) and transferred to nitrocellulose membrane using standard techniques. The membrane was then incubated with Blocking Buffer: 4% (w/v) non-fat milk in 50 mM TRIS-buffered saline (pH 7.5)/0.1% (v/v) Tween-20 (TBST) for 1 hr at room temperature with shaking. The membrane was subsequently incubated with rabbit anti-human β-glucocerebrosidase polyclonal primary antibodies (raised against a 19 amino acid peptide corresponding to C-terminus of human acid β-glucocerebrosidase; Sigma G-4171) diluted 1:2500 in Blocking Buffer for 1 hr at room temp or overnight at 4° C. with shaking. The blot was then washed with TBST at room temp with shaking and at least three buffer changes over 1 hr. The blot was then incubated with an enzyme-linked secondary antibody (e.g., horseradish peroxidase-conjugated goat anti-rabbit antibodies) diluted 1:10,000 in Blocking Buffer for 1 hr at room temp with shaking. The blot was washed with TB ST at room temp with shaking and at least three buffer changes over 1 hr. The blot was then incubated with chemiluminescence substrate (e.g., Pierce's Supersignal West-Dura Extended Duration Substrate™) for 5 min at room temp and visualized by an imaging system or by film to assess the level of protein expression for wild-type and variant acid β-glucocerebrosidase enzymes.

To assess β-glucocerebrosidase protein stability, the transiently expressed variant, recombinant β-glucocerebrosidase proteins and the purified wild-type, recombinant β-glucocerebrosidase protein (i.e. Cerezyme™) were incubated in neutral pH buffer at 37° C. and assayed for enzyme activity to determine the extent of loss of catalytic activity over a period of about three hours. Briefly, 60 μl of conditioned medium (containing individual variant, recombinant β-glucocerebrosidase proteins) was harvested after 24 or 48 hrs post-transfection and added to 420 μl of 0.1 M potassium phosphate (pH 7.5)/0.2% (v/v) Triton X-100/0.2% (w/v) BSA in 0.5 ml microfuge tubes. Similarly, purified wild-type, recombinant β-glucocerebrosidase protein was serially diluted to 1:12,500 in DMEM medium/10% FBS and 60 μl of this diluted wild-type, recombinant β-glucocerebrosidase protein sample was added to 420 μl 0.1 M potassium phosphate (pH 7.5)/0.2% (v/v) Triton X-100/0.2% (w/v) BSA to obtain a final dilution of 1:100,000. (This amount of wild-type, recombinant β-glucocerebrosidase protein was empirically determined to contain similar amounts of enzymatic activity as transiently expressed recombinant β-glucocerebrosidase proteins). All samples were incubated in a 37° C. waterbath and 70 μl of each sample was removed at specified time points (0, 30, 60, 90, 120 or 180 min) and added to new 0.5 ml microcentrifuge tubes containing 20 μl of 0.5 M NaOAc (pH 5.2). The samples were mixed thoroughly and 25 μl of each diluted sample was used to measure the residual recombinant β-glucocerebrosidase protein enzyme activity (in triplicate) as described above. The initial enzyme activity (at t=0 min) was designated as 100% for each recombinant β-glucocerebrosidase protein while the enzymatic activities for all subsequent time points were normalized to the initial activity to determine the residual enzyme activity over the entire time course. Data from multiple experiments (at least 2 separate experiments) were used to obtain average values for residual recombinant β-glucocerebrosidase protein activity for individual time points and graphed relative to incubation time as shown.

Example 2

The expression of variant, recombinant β-glucocerebrosidase proteins with specific amino acid substitutions were compared to wild-type, recombinant β-glucocerebrosidase protein ("wild-type GlcCerase") using transient transfection experiments described above (FIG. 1). As can be seen in FIG. 1A, the variant, recombinant β-glucocerebrosidase protein with the F316A and L317F variations ("GlcCerase-F316A/L317F"), the variant, recombinant β-glucocerebrosidase protein with the K321N variation ("GlcCerase-K321N"), the variant, recombinant β-glucocerebrosidase protein with the H145L variation ("GlcCerase-H145L"), the variant, recombinant β-glucocerebrosidase proteins with the F316A, L317F and K321N variations ("GlcCerase-F316A/L317F/K321N"), the variant, recombinant β-glucocerebrosidase proteins with the H145L and K321N variations ("GlcCerase-H145L/K321N") were transiently expressed with the wild-type GlcCerase in HEK293T cells. The conditioned cell culture medium was harvested 48 hrs after transfection and assayed for β-glucocerebrosidase enzyme activity using the 4-methylumbelliferyl-β-D-glucoside (4-MUG) fluorogenic substrate to assess the relative level of expression of these variant GlcCerase enzymes compared to wild-type GlcCerase. These results show that different variant GlcCerase enzymes were expressed as well or better than wild-type GlcCerase as evidenced by the higher measured enzyme activity in cell culture medium. Other variant GlcCerase enzymes including GlcCerase-H145F, GlcCerase-H145L/F316A/L317F/K321N were also expressed better than wild-type GlcCerase (data not shown). GlcCerase-K321A and GlcCerase-H145F/F316A/L317F/K321N were expressed at approximately the same level as wild-type GlcCerase while GlcCerase-K321V was expressed less efficiently than wild-type GlcCerase (data not shown).

The amount of variant GlcCerase proteins and wild-type GlcCerase protein present in conditioned cell culture medium was evaluated using Western blotting as described above. As can be seen in FIG. 1B, higher amounts of GlcCerase-F316A/L317F and GlcCerase-K321N proteins were present in conditioned cell culture medium than wild-type GlcCerase. These Western blotting data are consistent with the GlcCerase enzyme activity results and confirm that certain variant GlcCerase enzymes are expressed and secreted better than wild-type GlcCerase. Similar results were observed for other variant GlcCerase proteins (data not shown).

Example 3

Figure 2:
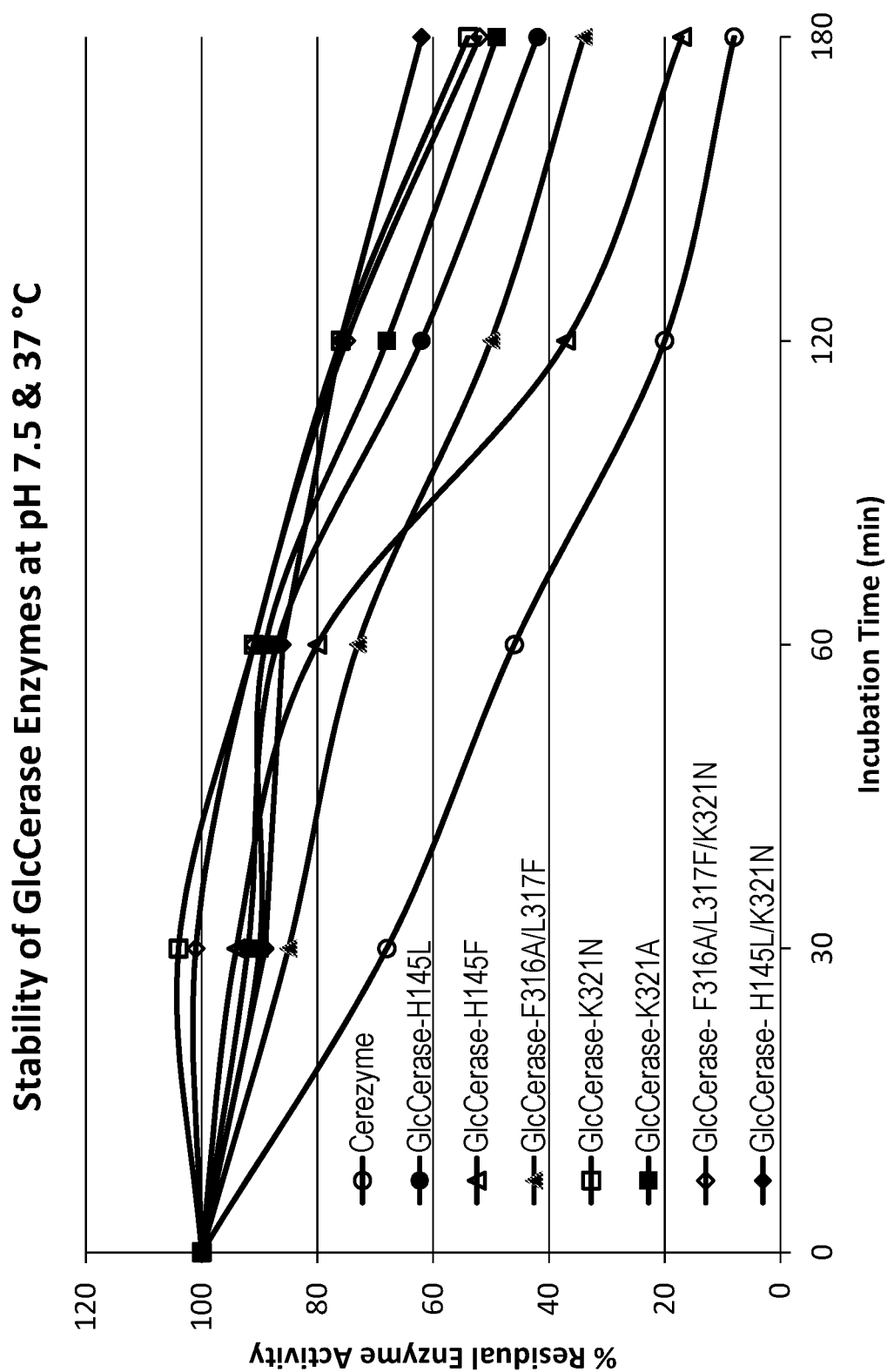
FIG. 2 shows the stability of variant, recombinant β-glucocerebrosidase proteins with the H145L modification, the H145F modification, the F316A/L317F modifications, the K321N modification, the K321A modification, the F316A/L317F/K321N modifications, and the H145L/K321N modifications compared to wild-type, recombinant β-glucocerebrosidase protein at pH 7.5 and 37° C.

The variant, recombinant β-glucocerebrosidase protein with the F316A and L317F variations ("GlcCerase-F316A/L317F") was compared to purified wild-type, recombinant β-glucocerebrosidase protein ("wild-type GlcCerase") using the in vitro stability assay described above. The conditions used for the variant and wild-type proteins were identical. As can be seen in FIG. 2, GlcCerase-F316A/L317F is significantly more stable than wild-type GlcCerase at about neutral pH and about 37° C. over a two or three hour time course. GlcCerase-F316A/L317F retained 85% of its initial activity after 30 minutes of incubation. GlcCerase-F316A/L317F retained 73% of its initial activity after 60 minutes of incubation. GlcCerase-F316A/L317F retained 50% of its initial activity after 120 minutes of incubation. GlcCerase-F316A/L317F retained 34% of its initial activity after 180 minutes of incubation. By comparison, wild-type GlcCerase treated under the same experimental conditions retained 68% of its initial activity after 30 minutes of incubation. Wild-type GlcCerase retained 46% of its initial activity after 60 minutes of incubation. Wild-type GlcCerase retained 20% of its initial activity after 120 minutes of incubation. Wild-type GlcCerase retained 8% of its initial activity after 180 minutes of incubation.

Figure 3:
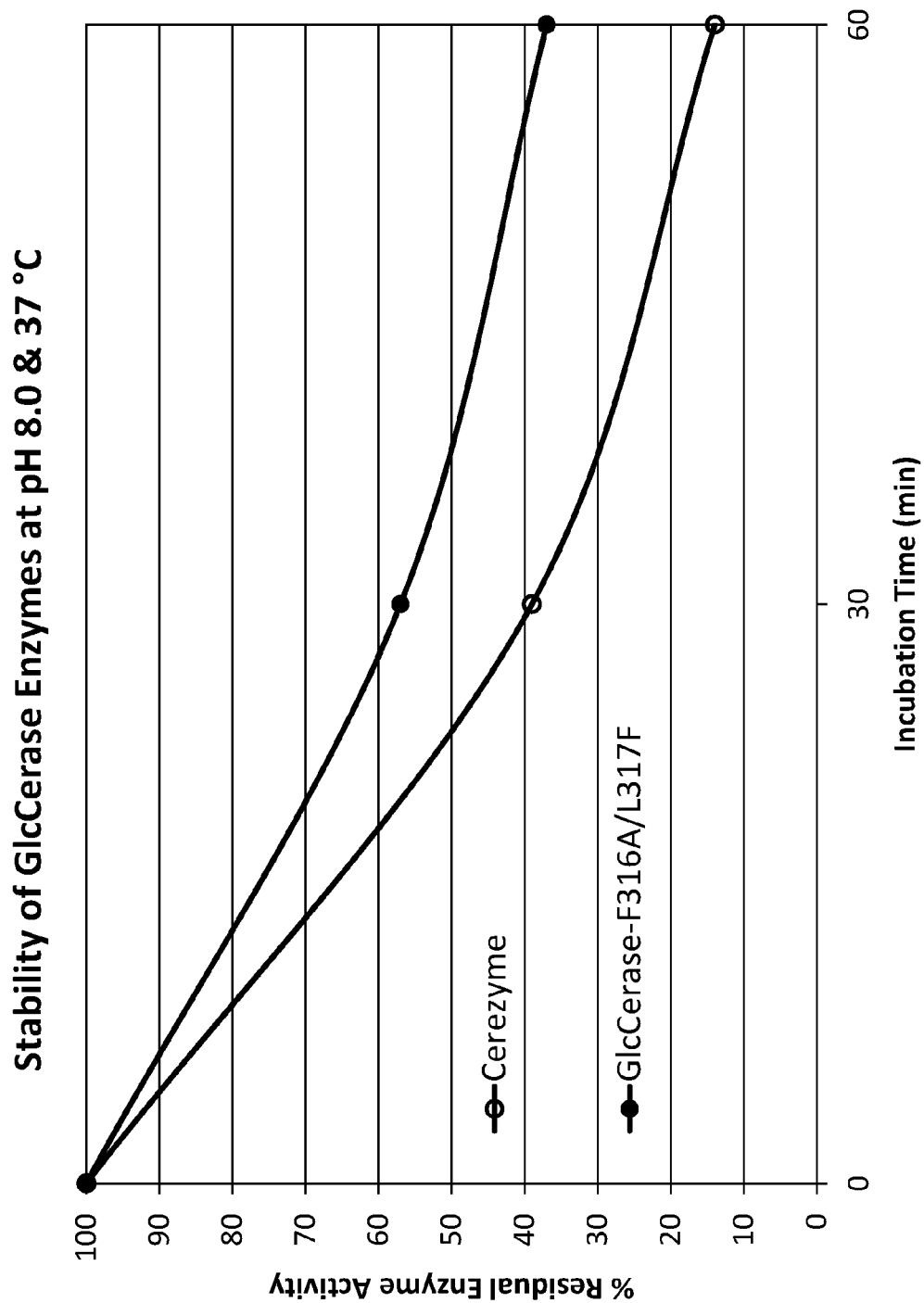
FIG. 3 shows the stability of the variant, recombinant β-glucocerebrosidase protein with the F316A/L317F modifications compared to wild-type, recombinant β-glucocerebrosidase protein at pH 8 and 37° C.

The estimated half-life (operationally defined in this study as the incubation time at about pH 7.5 and about 37° C. that resulted in a 50% loss of initial enzyme activity) for GlcCerase-F316A/L317F is approximately 120 minutes while the estimated half-life for wild-type GlcCerase is approximately 50 minutes under these experimental conditions. GlcCerase-F316A/L317F was also tested at about pH 8 and about 37° C. and displayed a similar trend (FIG. 3). Both GlcCerase-F316A/L317F and wild-type GlcCerase were less stable at about pH 8 and about 37° C., but these results confirm that GlcCerase-F316A/L317F is more stable at higher pH than wild-type GlcCerase.

Example 4

The variant, recombinant β-glucocerebrosidase protein with the K321N variation ("GlcCerase-K321N") was compared to purified wild-type, recombinant β-glucocerebrosidase protein ("wild-type GlcCerase") using the assay described above. The conditions used for the variant and wild-type proteins were identical. As can be seen in FIG. 2, GlcCerase-K321N is significantly more stable than wild-type GlcCerase at about neutral pH and about 37° C. over a three hour time course. GlcCerase-K321N retained 104% of its initial activity after 30 minutes of incubation. GlcCerase-K321N retained 91% of its initial activity after 60 minutes of incubation. GlcCerase-K321N retained 76% of its initial activity after 120 minutes of incubation. GlcCerase-K321N retained 54% of its initial activity after 180 minutes of incubation. By comparison, wild-type GlcCerase treated under the same experimental conditions retained 68% of its initial activity after 30 minutes of incubation. Wild-type GlcCerase retained 46% of its initial activity after 60 minutes of incubation. Wild-type GlcCerase retained 20% of its initial activity after 120 minutes of incubation. Wild-type GlcCerase retained 8% of its initial activity after 180 minutes of incubation.

The estimated half-life (operationally defined in this study as the incubation time at about pH 7.5 and about 37° C. that resulted in a 50% loss of initial enzyme activity) for GlcCerase-K321N is approximately 180 minutes while the estimated half-life for wild-type GlcCerase is approximately 50 minutes under these experimental conditions.

Example 5

The variant, recombinant β-glucocerebrosidase protein with the H145L variation ("GlcCerase-H145L") was compared to purified wild-type, recombinant β-glucocerebrosidase protein ("wild-type GlcCerase") using the assay described above. The conditions used for the variant and wild-type proteins were identical. As can be seen in FIG. 2, GlcCerase-H145L is significantly more stable than wild-type GlcCerase at about neutral pH and about 37° C. over a three hour time course. GlcCerase-H145L retained 92% of its initial activity after 30 minutes of incubation. GlcCerase-H145L retained 87% of its initial activity after 60 minutes of incubation. GlcCerase-H145L retained 62% of its initial activity after 120 minutes of incubation. GlcCerase-H145L retained 42% of its initial activity after 180 minutes of incubation. By comparison, wild-type GlcCerase treated under the same experimental conditions retained 68% of its initial activity after 30 minutes of incubation. Wild-type GlcCerase retained 46% of its initial activity after 60 minutes of incubation. Wild-type GlcCerase retained 20% of its initial activity after 120 minutes of incubation. Wild-type GlcCerase retained 8% of its initial activity after 180 minutes of incubation.

The estimated half-life (operationally defined in this study as the incubation time at about pH 7.5 and about 37° C. that resulted in a 50% loss of initial enzyme activity) for GlcCerase-H145L is approximately 160 minutes while the estimated half-life for wild-type GlcCerase is approximately 50 minutes under these experimental conditions.

Example 6

The variant, recombinant β-glucocerebrosidase protein with the H145F variation ("GlcCerase-H145F") was compared to purified wild-type, recombinant β-glucocerebrosidase protein ("wild-type GlcCerase") using the assay described above. The conditions used for the variant and wild-type proteins were identical. As can be seen in FIG. 1, GlcCerase-H145F is significantly more stable than wild-type GlcCerase at about neutral pH and about 37° C. over a three hour time course. GlcCerase-H145F retained 94% of its initial activity after 30 minutes of incubation. GlcCerase-H145F retained 80% of its initial activity after 60 minutes of incubation. GlcCerase-H145F retained 37% of its initial activity after 120 minutes of incubation. GlcCerase-H145F retained 17% of its initial activity after 180 minutes of incubation. By comparison, wild-type GlcCerase treated under the same experimental conditions retained 68% of its initial activity after 30 minutes of incubation. Wild-type GlcCerase retained 46% of its initial activity after 60 minutes of incubation. Wild-type GlcCerase retained 20% of its initial activity after 120 minutes of incubation. Wild-type GlcCerase retained 8% of its initial activity after 180 minutes of incubation.

The estimated half-life (operationally defined in this study as the incubation time at about pH 7.5 and about 37° C. that resulted in a 50% loss of initial enzyme activity) for GlcCerase-H145F is approximately 100 minutes while the estimated half-life for wild-type GlcCerase is approximately 50 minutes under these experimental conditions.

Example 7

The variant, recombinant β-glucocerebrosidase protein with the F316A, L317F, and K321N variations ("GlcCerase-F316A/L317F/K321N") was compared to purified wild-type, recombinant β-glucocerebrosidase protein ("wild-type GlcCerase") using the assay described above. The conditions used for the variant and wild-type proteins were identical. As can be seen in FIG. 2, GlcCerase-F316A/L317F/K321N is significantly more stable than wild-type GlcCerase at about neutral pH and about 37° C. over a three hour time course. GlcCerase-F316A/L317F/K321N retained 101% of its initial activity after 30 minutes of incubation. GlcCerase-F316A/L317F/K321N retained 91% of its initial activity after 60 minutes of incubation. GlcCerase-F316A/L317F/K321N retained 75% of its initial activity after 120 minutes of incubation. GlcCerase-F316A/L317F/K321N retained 52% of its initial activity after 180 minutes of incubation. By comparison, wild-type GlcCerase treated under the same experimental conditions retained 68% of its initial activity after 30 minutes of incubation. Wild-type GlcCerase retained 46% of its initial activity after 60 minutes of incubation. Wild-type GlcCerase retained 20% of its initial activity after 120 minutes of incubation. Wild-type GlcCerase retained 8% of its initial activity after 180 minutes of incubation.

The estimated half-life (operationally defined in this study as the incubation time at about pH 7.5 and about 37° C. that resulted in a 50% loss of initial enzyme activity) for GlcCerase-F316A/L317F/K321N is approximately 180 minutes while the estimated half-life for wild-type GlcCerase is approximately 50 minutes under these experimental conditions.

Example 8

The variant, recombinant β-glucocerebrosidase protein with the H145L, F316A and L317F variations ("GlcCerase-H145L/F316A/L317F") was compared to purified wild-type, recombinant β-glucocerebrosidase protein ("wild-type GlcCerase") using the assay described above. The conditions used for the variant and wild-type proteins were identical. GlcCerase-H145L/F316A/L317F is significantly more stable than wild-type GlcCerase at about neutral pH and about 37° C. over a three hour time course. GlcCerase-H145L/F316A/L317F retained approximately 77% of its initial activity after 30 minutes of incubation. GlcCerase-H145L/F316A/L317F N retained 80% of its initial activity after 60 minutes of incubation. GlcCerase-H145L/F316A/L317F retained 56% of its initial activity after 120 minutes of incubation. GlcCerase-H145L/F316A/L317F retained 39% of its initial activity after 180 minutes of incubation. By comparison, wild-type GlcCerase treated under the same experimental conditions retained 68% of its initial activity after 30 minutes of incubation. Wild-type GlcCerase retained 46% of its initial activity after 60 minutes of incubation. Wild-type GlcCerase retained 20% of its initial activity after 120 minutes of incubation. Wild-type GlcCerase retained 8% of its initial activity after 180 minutes of incubation.

The estimated half-life (operationally defined in this study as the incubation time at about pH 7.5 and about 37° C. that resulted in a 50% loss of initial enzyme activity) for GlcCerase-H145L/F316A/L317F is approximately 135 minutes while the estimated half-life for wild-type GlcCerase is approximately 50 minutes under these experimental conditions.

Example 9

The variant, recombinant β-glucocerebrosidase protein with the H145L and K321N variations ("GlcCerase-H145L/K321N") was compared to purified wild-type, recombinant β-glucocerebrosidase protein ("wild-type GlcCerase") using the assay described above. The conditions used for the variant and wild-type proteins were identical. As can be seen in FIG. 2, GlcCerase-H145L/K321N is significantly more stable than wild-type GlcCerase at about neutral pH and about 37° C. over a three hour time course. GlcCerase-H145L/K321N retained 89% of its initial activity after 30 minutes of incubation. GlcCerase-H145L/K321N retained 86% of its initial activity after 60 minutes of incubation. GlcCerase-H145L/K321N retained 76% of its initial activity after 120 minutes of incubation. GlcCerase-H145L/K321N retained 62% of its initial activity after 180 minutes of incubation. By comparison, wild-type GlcCerase treated under the same experimental conditions retained 68% of its initial activity after 30 minutes of incubation. Wild-type GlcCerase retained 46% of its initial activity after 60 minutes of incubation. Wild-type GlcCerase retained 20% of its initial activity after 120 minutes of incubation. Wild-type GlcCerase retained 8% of its initial activity after 180 minutes of incubation.

The estimated half-life (operationally defined in this study as the incubation time at about pH 7.5 and about 37° C. that resulted in a 50% loss of initial enzyme activity) for GlcCerase-H145L/K321N is approximately 180 minutes while the estimated half-life for wild-type GlcCerase is approximately 50 minutes under these experimental conditions.

Example 10

The variant, recombinant β-glucocerebrosidase protein with the K321A variation ("GlcCerase-K321A") was compared to purified wild-type, recombinant β-glucocerebrosidase protein ("wild-type GlcCerase") using the assay described above. The conditions used for the variant and wild-type proteins were identical. As can be seen in FIG. 2, GlcCerase-K321A is significantly more stable than wild-type GlcCerase at about neutral pH and about 37° C. over a three hour time course. GlcCerase-K321A retained 90% of its initial activity after 30 minutes of incubation. GlcCerase-K321A retained 89% of its initial activity after 60 minutes of incubation. GlcCerase-K321A retained 68% of its initial activity after 120 minutes of incubation. GlcCerase-K321A retained 49% of its initial activity after 180 minutes of incubation. By comparison, wild-type GlcCerase treated under the same experimental conditions retained 68% of its initial activity after 30 minutes of incubation. Wild-type GlcCerase retained 46% of its initial activity after 60 minutes of incubation. Wild-type GlcCerase retained 20% of its initial activity after 120 minutes of incubation. Wild-type GlcCerase retained 8% of its initial activity after 180 minutes of incubation.

The estimated half-life (operationally defined in this study as the incubation time at about pH 7.5 and about 37° C. that resulted in a 50% loss of initial enzyme activity) for Glc-Cerase-K321A is approximately 170 minutes while the estimated half-life for wild-type GlcCerase is approximately 50 minutes under these experimental conditions.

Example 11

The variant, recombinant β-glucocerebrosidase protein with the K321A variation ("GlcCerase-K321V") was compared to purified wild-type, recombinant β-glucocerebrosidase protein ("wild-type GlcCerase") using the assay described above. The conditions used for the variant and wild-type proteins were identical. GlcCerase-K321V is significantly more stable than wild-type GlcCerase at about neutral pH and about 37° C. over a three hour time course. GlcCerase-K321V retained 74% of its initial activity after 30 minutes of incubation. GlcCerase-K321V retained 55% of its initial activity after 60 minutes of incubation. Glc-Cerase-K321V retained 29% of its initial activity after 120 minutes of incubation. GlcCerase-K321V retained 15% of its initial activity after 180 minutes of incubation. By comparison, wild-type GlcCerase treated under the same experimental conditions retained 68% of its initial activity after 30 minutes of incubation. Wild-type GlcCerase retained 46% of its initial activity after 60 minutes of incubation. Wild-type GlcCerase retained 20% of its initial activity after 120 minutes of incubation. Wild-type Glc-Cerase retained 8% of its initial activity after 180 minutes of incubation.

The estimated half-life (operationally defined in this study as the incubation time at about pH 7.5 and about 37° C. that resulted in a 50% loss of initial enzyme activity) for Glc-Cerase-K321V is approximately 70 minutes while the estimated half-life for wild-type GlcCerase is approximately 50 minutes under these experimental conditions.

The above results are summarized in Table 1

TABLE 1

| Recombinant GlcCerase protein | n = | Residual Activity (3 hr) | Estimated half-life | Fold-improvement |
| --- | --- | --- | --- | --- |
| Wild-type | 7 | 8% | ~50 min | — |
| H145L | 4 | 42% | ~160 min | 3.2 |
| H145F | 2 | 17% | ~100 min | 2.0 |
| F316A/L317F | 4 | 34% | ~120 min | 2.4 |
| K321N | 4 | 54% | >180 min | >3.6 |
| K321A | 2 | 49% | ~170 min | 3.4 |
| K321V | 1 | 15% | ~70 min | 1.4 |
| F316A/L317F/K321N | 5 | 52% | >180 min | >3.6 |
| H145L/F316A/L317F | 1 | 39% | ~135 min | 2.7 |
| H145L/K321N | 2 | 62% | >180 min | >3.6 |

Residual activity is the amount of enzyme activity that remains after the three hour incubation and expressed as the percent of initial enzyme activity (at t=0 min) for each variant, recombinant β-glucocerebrosidase protein in the stability assay. Each recombinant β-glucocerebrosidase protein was tested in at least two separate experiments (indicated by n in Table 1) to determine the average residual activities during the three hour time course except for GlcCerase-K321V and GlcCerase-H145L/F316A/L317F which were only tested once. The fold-improvement refers to the increase in the apparent half-lives of the variant, recombinant GlcCerase proteins relative to purified wild-type, recombinant GlcCerase protein.

The variant, recombinant β-glucocerebrosidase protein that has an amino acid variation at position 145, 316, 317, or 321, or GlcCerase-F316A/L317F, GlcCerase-K321N, GlcCerase-K321A, GlcCerase-K321V, GlcCerase-H145L, GlcCerase-H145F, or GlcCerase-F316A/L317F/K321N or GlcCerase-F316A/L317F/K321A or GlcCerase-F316A/L317F/K321V or GlcCerase-H145L/F316A/L317F or Glc-Cerase-H145L/K321N which can be characterized as retaining more catalytic activity relative to wild-type, recombinant β-glucocerebrosidase could be made in yeast cells, plant cells, mammalian cells or transgenic animals using molecular biology and protein purification techniques known to persons skilled in the art.

A composition comprising the variant, recombinant β-glucocerebrosidase protein that has an amino acid variation at position 145, 316, 317, or 321, or GlcCerase-F316A/L317F, GlcCerase-K321N, GlcCerase-K321A, GlcCerase-K321V, GlcCerase-H145L, GlcCerase-H145F, or GlcCerase-F316A/L317F/K321N or GlcCerase-F316A/L317F/K321A or GlcCerase-F316A/L317F/K321V or Glc-Cerase-H145L/F316A/L317F or GlcCerase-H145L/K321N and a pharmaceutically acceptable carrier could be made using pharmaceutically acceptable carriers known to persons skilled in the art.

A composition comprising the variant, recombinant β-glucocerebrosidase protein that has an amino acid variation at position 145, 316, 317, or 321, or GlcCerase-F316A/L317F, GlcCerase-K321N, GlcCerase-K321A, GlcCerase-K321V, GlcCerase-H145L, GlcCerase-H145F, or GlcCerase-F316A/L317F/K321N or GlcCerase-F316A/L317F/K321A or GlcCerase-F316A/L317F/K321V or Glc-Cerase-H145L/F316A/L317F or GlcCerase-H145L/K321N and a pharmaceutically acceptable buffer could be made using pharmaceutically acceptable buffers known to persons skilled in the art.

Example 12

Since GlcCerase protein is stable at acidic pH and very efficient at clearing the accumulated glucosylceramide substrate within lysosomes, one can develop a more stable GlcCerase ERT which can better withstand the unfavorable (neutral pH) environment to retain its catalytic activity so that a larger quantity of active drug is delivered to lysosomes for improved efficacy. The GlcCerase enzyme can be stabilized at about neutral pH when bound (and inhibited) by the active site enzyme inhibitor isofagomine (IFG). Protein stability for recombinant GlcCerase at about neutral pH is significantly improved with IFG as evidenced by an increase of up to 15° C. in the thermal melting temperature (Tm). The mechanism of action for IFG-induced GlcCerase stabilization is believed to result from the extensive hydrogen bonding network between IFG and six GlcCerase active site residues to restrict the unfolding of the active site and surrounding regions to maintain a more stable GlcCerase conformation. Maintaining the proper GlcCerase structure at the active site and surrounding regions helps catalytic activity and overall GlcCerase stability. A number of different modifications to GlcCerase can help retain catalytic activity and maintain a more stable protein structure at about neutral pH. Herein is provided the construction of a series of different GlcCerase enzymes with specific amino acid substitutions at strategic locations within loop structures near the active site to help form a more-ordered region near the active site that are less prone to unwinding at about neutral pH. Additionally, herein are provided modifications to an α-helix near the active site which may help to move this helix and an adjacent loop away from the catalytic site to maintain an open, active conformation.

An approach was utilized to generate a series of modified GlcCerase enzymes that were predicted to have superior protein stability than wild-type GlcCerase. Primarily, two different but complimentary strategies were used: (1) modification of certain loops and helices near the catalytic site to mimic the preferred, active GlcCerase conformations without actually inhibiting the enzyme; and, (2) modification of a random coil region which may enhance interactions between different residues and secondary structures for improved protein stability.

In one example, several residues were modified within the loop1 region (positions 311-319) to help form a more-ordered region near the active site that would be less prone to unwinding at about neutral pH. This variant (GlcCerase-F316A/L317F) with modifications within loop1 was shown to be significantly more stable than GlcCerase at about pH 7.5 and 37° C.

In a second example, an α-helix near the active site (α6) was modified that was intended to stabilize this helix and help pull an adjacent loop (loop1) away from the catalytic site to maintain an open, active conformation. Thus, modified GlcCerase enzymes were generated that contained an amino acid substitution at position 321 to replace a charged lysine residue with an uncharged residue within helix α6 to promote more hydrophobic interactions with adjacent α-helices and β-structures to stabilize the protein. Protein alignments were analyzed for GlcCerase enzymes for various species (Table II) and noted that a GlcCerase homolog of *B. taurus* (bull GlcCerase; accession code DAA31806.1) contained asparagine at position 321 ($^{321}$Asn). This suggests that lysine at position 321 ($^{321}$Lys) may be potentially be replaced with a different amino acid residue without abolishing GlcCerase catalytic activity. GlcCerase-K321N retained approximately 75% and 54% of its original catalytic activity at about pH 7.5 and 37° C. after 2 and 3 hrs, respectively. In contrast, wild-type GlcCerase retained only 21% and 8% of its initial activity under the same conditions. The estimated half-life of GlcCerase-K321N was approximately 3.5-fold longer than wild-type GlcCerase. Similarly, GlcCerase-K321A retained approximately 68% and 49% of its original catalytic activity at about pH 7 and 37° C. after 2 and 3 hrs, respectively. The estimated half-life of GlcCerase-K321A was approximately 3-fold longer than wild-type GlcCerase. GlcCerase-K321V retained approximately 29% and 15% of its original catalytic activity at about pH 7 and 37° C. after 2 and 3 hrs, respectively. The estimated half-life of GlcCerase-K321V was approximately 1.4-fold longer than wild-type GlcCerase. These data show that removing a positively-charged lysine residue within helix α6 made this region more ordered to limit unwinding of this region to confer greater GlcCerase protein stability.

In a third example, a random coil region was modified between a beta-sheet (β2) and an α-helix (α2) which may facilitate better interactions between different residues and secondary structures for improved stability. Protein alignment analysis of GlcCerase enzymes from various species (Table 2) revealed that position 145 within this random coil was divergent among the different species. A *B. taurus* homolog and *S. scrofa* (pig) both contain leucine at this position while murine GlcCerase contains serine. Thus, we substituted histidine at position 145 ($^{145}$His) with either Leu (H145L) or Phe (H145F) to determine whether these modifications would improve GlcCerase stability. GlcCerase-H145L GlcCerase was shown to be more stable than wild-type GlcCerase and retained 62% of its initial activity after 2 hrs and 42% after 3 hrs with an estimated half-life of approximately 3-fold longer half-life than wild-type GlcCerase (160 min vs. 50 min). Similarly, GlcCerase H145F retained approximately 37% after 2 hrs of its initial activity and 17% after 3 hrs with an approximately 2-fold longer half-life relative to wild-type GlcCerase. It is not currently known how these modifications affected the GlcCerase structure but it is possible that replacing a partially charged residue ($^{145}$His) with either leucine or phenylalanine hydrophobic residue would make this region more ordered to limit unwinding of this region. Alternatively, these modifications may create a turn and enhance interactions between secondary structures (e.g., beta-sheet (32 and helix α2).

Protein alignment data is summarized in Table 2

TABLE 2

| | | |
|---|---|---|
| Human GlcCerase | $^{140}$DDFQLHNFSLPEEDT SEQ ID NO: 17 | $^{315}$DFLAPAKATLGET SEQ ID NO: 21 |
| S. scorfa GlcCerase | $^{140}$DDFQLLNFSLPEEDV SEQ ID NO: 18 | $^{315}$DFLAPAKATLGET SEQ ID NO: 22 |
| B taurus GlcCerase | $^{140}$DDFQLLNFSLPEEDV SEQ ID NO: 19 | $^{315}$DFLAPANATLGET SEQ ID NO: 23 |
| Murine GlcCerase | $^{140}$NDFQLSNFSLPEEDT SEQ ID NO: 20 | $^{315}$DFLAPAKATLGET SEQ ID NO: 24 |

Suitable variant, recombinant β-glucocerebrosidase proteins can also have one or more replacement amino acids in the loop1 region of the protein, the one or more replacement amino acids characterized as having a side-chain conformation that increases order near the active site of the protein. These proteins can also have one or more replacement amino acids in the loop1 region of the protein, the one or more replacement amino acids characterized as having a side-chain conformation that increases order near the active site of the protein is characterized as being more stable at a range of from about pH3 to about pH8 compared to wild-type, recombinant β-glucocerebrosidase protein. These proteins can also have one or more replacement amino acids in the loop1 region of the protein, the one or more replacement amino acids characterized as having a side-chain conformation that increases order near the active site of the protein is characterized as being more stable at about neutral pH compared to wild-type, recombinant β-glucocerebrosidase protein. These proteins can also have one or more replacement amino acids in the loop1 region of the protein, the one or more replacement amino acids is characterized as being less prone to unwinding at a range of from about pH3 to about pH8 compared to wild-type, recombinant β-glucocerebrosidase protein. These proteins can also have one or more replacement amino acids in the loop1 region of the protein, the one or more replacement amino acids is characterized as being less prone to unwinding at about neutral pH compared to wild-type, recombinant β-glucocerebrosidase protein.

Suitable variant, recombinant β-glucocerebrosidase proteins can also have one or more replacement amino acids in the α-helix near the active site (α6) of the protein, the one or more replacement amino acid sides characterized as having a side-chain confirmation that stabilizes this helix and pulls adjacent loop1 away from the catalytic site and has an open and active conformation. These proteins can also have one or more replacement amino acids in the α-helix near the active site (α6) of the protein, the one or more replacement amino acid sides characterized as having a side-chain confirmation that stabilizes this helix and pulls adjacent loop1 away from the catalytic site and has an open and active conformation is characterized as being more stable at a range of from about pH3 to about pH8 compared to wild-type, recombinant β-glucocerebrosidase protein. These proteins can also be characterized as having a more open conformation at about neutral pH compared to wild-type, recombinant β-glucocerebrosidase protein. These proteins can also have one or more replacement amino acids in the loop1 region of the protein, the one or more replacement amino acids is characterized as having a more open conformation at a range of from about pH3 to about pH8 compared to wild-type, recombinant β-glucocerebrosidase protein. These proteins can also have one or more replacement amino acids in the loop1 region of the protein, the one or more replacement amino acids characterized as having a more open conformation at about neutral pH compared to wild-type, recombinant β-glucocerebrosidase protein.

Suitable variant, recombinant β-glucocerebrosidase protein can also have one or more replacement amino acids in the random coil region between beta-sheet (β2) and an α-helix (α2), the one or more replacement amino acid side-chains characterized as having a side-chain confirmation that facilitates better interactions between different residues and secondary structures for improved stability. These proteins can also have one or more replacement amino acids in the random coil region between beta-sheet (β2) and an α-helix (α2), the one or more replacement amino acid side-chains characterized as having a side-chain confirmation that facilitates better interactions between different residues and secondary structures for improved stability is characterized as being more stable at a range of from about pH3 to about pH8 compared to wild-type, recombinant β-glucocerebrosidase protein. These proteins can also have one or more replacement amino acids in the random coil region between beta-sheet (β2) and an α-helix (α2), the one or more replacement amino acid side-chains characterized as having a side-chain confirmation that facilitates better interactions between different residues and secondary structures for improved stability at about neutral pH compared to wild-type, recombinant β-glucocerebrosidase protein. These proteins can also have one or more replacement amino acids in the random coil region between beta-sheet (β2) and an α-helix (α2), the one or more replacement amino acid side-chains characterized as having a side-chain confirmation that facilitates better interactions between different residues and secondary structures for improved stability at a range of from about pH3 to about pH8 compared to wild-type, recombinant β-glucocerebrosidase protein. These proteins can also have one or more replacement amino acids in the random coil region between beta-sheet (β2) and an α-helix (α2), the one or more replacement amino acid side-chains characterized as having a side-chain confirmation that facilitates better interactions between different residues and secondary structures for improved stability at about neutral pH compared to wild-type, recombinant β-glucocerebrosidase protein.

Suitable methods for treating a lysosomal storage disease can also include administering to a subject in need thereof a variant, recombinant β-glucocerebrosidase protein characterized as having increased stability compared to wild-type, recombinant β-glucocerebrosidase is provided. Methods for treating a lysosomal storage disease can also include administering to a subject in need thereof a variant, recombinant β-glucocerebrosidase protein characterized as retaining increased catalytic activity compared to wild-type, recombinant β-glucocerebrosidase. Methods for treating a lysosomal storage disease can also include administering to a subject in need thereof a variant, recombinant β-glucocerebrosidase protein characterized as having an increased specific activity compared to wild-type, recombinant β-glucocerebrosidase.

Methods for treating a lysosomal storage disease can also include administering to a subject in need thereof a variant, recombinant β-glucocerebrosidase protein having an amino acid variation at one or more of the following positions: 316, 317, 321 and 145. Methods for treating a lysosomal storage disease can also include administering to a subject in need thereof a variant, recombinant β-glucocerebrosidase protein with the amino acid variations 316A and L317F. Methods for treating a lysosomal storage disease can also include administering to a subject in need thereof a variant, recombinant β-glucocerebrosidase protein with the amino acid variation K321N. Methods for treating a lysosomal storage disease can also include administering to a subject in need thereof a variant, recombinant β-glucocerebrosidase protein with the amino acid variation K321A. Methods for treating a lysosomal storage disease can also include administering to a subject in need thereof a variant, recombinant β-glucocerebrosidase protein with the amino acid variation K321V. Methods for treating a lysosomal storage disease can also include administering to a subject in need thereof a variant, recombinant β-glucocerebrosidase protein with the amino acid variation H145L. Methods for treating a lysosomal storage disease can also include administering to a subject in need thereof a variant, recombinant β-glucocerebrosidase protein with the amino acid variation H145F. Methods for treating a lysosomal storage disease can also include administering to a subject in need thereof a variant, recombinant β-glucocerebrosidase protein with the amino acid variations F316A, L317F, and K321N. Methods for treating a lysosomal storage disease can also include administering to a subject in need thereof a variant, recombinant β-glucocerebrosidase protein with the amino acid variations F316A, L317F, and K321A. Methods for treating a lysosomal storage disease can also include administering to a subject in need thereof a variant, recombinant β-glucocerebrosidase protein with the amino acid variations F316A, L317F, and K321V. Methods for treating a lysosomal storage disease can also include administering to a subject in need thereof a variant, recombinant β-glucocerebrosidase protein with the amino acid variations H145L, F316A, and L317F. Methods for treating a lysosomal storage disease can also include administering to a subject in need thereof a variant, recombinant β-glucocerebrosidase protein with the amino acid variations H145L and K321N. Methods for treating a lysosomal storage disease can also include administering to a subject in need thereof a variant, recombinant β-glucocerebrosidase protein with the amino acid variations H145L and K321A. Methods for treating a lysosomal storage disease can also include administering to a subject in need thereof a variant, recombinant β-glucocerebrosidase protein with the amino acid variations H145L and K321V. Methods to treat the lysosomal storage disease can also include methods to treat Gaucher disease. Methods of treatment can be by intravenous infusion, by intramuscular injection or by other routes of administration known to one skilled in the art.

Suitable compounds can have a variant, recombinant β-glucocerebrosidase protein characterized as having any one of the following amino acid sequences: SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, or SEQ ID NO: 16. Suitable compounds can have a variant, recombinant β-glucocerebrosidase protein characterized as having any one of the following amino acid sequences: SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, or SEQ ID NO: 16.

Suitable variant, recombinant β-glucocerebrosidase proteins can also be characterized as capable of increased expression relative to wild-type, recombinant β-glucocerebrosidase. Variant, recombinant β-glucocerebrosidase protein expression can also be increased by at least about 10% relative to wild-type, recombinant β-glucocerebrosidase. Variant, recombinant β-glucocerebrosidase protein expression can also be increased by at least about 25% relative to wild-type, recombinant β-glucocerebrosidase. Variant, recombinant β-glucocerebrosidase protein expression can also be increased by at least about 50% relative to wild-type, recombinant β-glucocerebrosidase. Variant, recombinant β-glucocerebrosidase protein expression can also be increased by at least about 80% relative to wild-type, recombinant β-glucocerebrosidase. Variant, recombinant β-glucocerebrosidase proteins can also be capable of being expressed in mammalian cells, transgenic animals or in yeast cells. Variant, recombinant β-glucocerebrosidase protein can also be expressed in a human. Variant, recombinant β-glucocerebrosidase protein can also be expressed from an inserted gene.

Example 13

Variant, recombinant GlcCerase proteins and wild-type GlcCerase were expressed in cell culture according to methods mentioned previously to assess the relative expression of these variant GlcCerase enzymes compared to the wild-type GlcCerase. A number of different variant GlcCerase enzymes were expressed better than wild-type GlcCerase in transient transfection experiments as measured by enzyme activity from conditioned medium after about 48 hours post transfection (FIG. 1). GlcCerase-F316A/L317A was expressed better than wild-type GlcCerase (about 282%), GlcCerase-K321N was expressed better than wild-type GlcCerase (about 272%), GlcCerase-H145L was expressed better than wild-type GlcCerase (about 157%), GlcCerase-F316A/L317A/K321N was expressed better than wild-type GlcCerase (about 272%), GlcCerase-H145L/K321N was expressed better than wild-type GlcCerase (about 317%). GlcCerase-K321A was expressed equivalently as wild-type GlcCerase while GlcCerase-K321V was expressed at lower levels than wild-type (about 61%) (data not shown).

Also provided herein are methods of making a compound comprising a variant, recombinant β-glucocerebrosidase protein characterized as having any one of the following amino acid sequences: SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, or SEQ ID NO: 16. Also provided herein are methods of making a nucleic acid encoding a variant, recombinant β-glucocerebrosidase protein characterized as having any one of the following amino acid sequences: SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, or SEQ ID NO: 16.

Example 14

Plasmid Construction for Wild-Type and Modified GlcCerase Enzymes

DNA plasmids for the expression of wild-type and modified GlcCerase enzymes were generated using oligonucleotide primers (listed in Table 3) or synthetic DNA minigenes (>400 bp) encoding a fragment of GlcCerase with specific amino acid substitutions. All primers and synthetic DNA minigenes were purchased from Integrated DNA Technologies™ (Coralville, Iowa). Wild-type human GlcCerase (designated as pHD101) was constructed by generating GlcCerase cDNA by PCR and ligating into a mammalian expression vector. Briefly, the entire wild-type human GlcCerase cDNA was amplified with its natural Kozak sequence and stop codon using primers A & B and the human GlcCerase cDNA clone (Origene™) template DNA in two identical 50 μl reactions via Phusion-HF high-fidelity DNA Polymerase™ (NEB™) and 200 μM dNTPs. Primer A was constructed to contain a 5' BglII and an internal EcoRI restriction site that immediately preceded the Kozak sequence while primer B contained 3' NheI and NotI restriction sites that followed the stop codon to enable cloning of the PCR product into expression vectors. The PCR reactions were pooled and the resultant ~1.6 kilobase (kb) PCR product was separated and excised from a 1% (w/v) agarose preparative gel and isolated using QIAGEN's™ Gel Extraction kit. The PCR product was subsequently digested overnight with restriction endonucleases BglII and NotI at 37° C. and re-purified using QIAGEN's™ PCR cleanup kit per the manufacturer's instructions. The mammalian expression vector pEF6/V5-HisA™ was digested with BamHI and NotI, dephosphorylated using Antarctic Phosphatase™ and isolated using QIAGEN's™ PCR cleanup kit. The Bgl II-NotI digested PCR product (2 μl) was ligated into the BamHI-NotI pEF6/V5-HisA™ vector (1 μl) using T4 DNA ligase (NEB™) according to the manufacturer's instructions. Chemically-competent E. coli cells were transformed with 1 μl of the ligation reaction and plated onto Luria-Bertani (LB) agar plates containing 100 μg/ml ampicillin and incubated overnight at 37° C. to form distinct bacterial colonies that had been transformed with the plasmid DNA containing the β-lactamase gene to confer ampicillin resistance. Individual ampicillin-resistant bacterial colonies were picked and expanded in 4 ml LB broth (containing 100 μg/ml ampicillin) overnight at 37° C. and plasmid DNA was isolated on the following day by Miniprep™ (QIAGEN™) according to the manufacturer's instructions. The isolated plasmid DNAs were checked by two different restriction digest reactions using EcoRI & NheI and BamHI, respectively. A correct plasmid DNA from clone 4 (designated as pHD 101.4) was chosen and used to re-transform competent E. coli cells as described above for high-level replication of the plasmid DNA. A colony from a LB agar-ampicillin plate was then picked and grown in 200 ml LB broth overnight at 37° C. and plasmid pHD101.4 was isolated by Maxiprep™ (Promega™). Plasmid pHD101.4 (encoding wild-type human GlcCerase cDNA) was verified by DNA sequencing and used for the construction of other GlcCerase enzymes and for transient transfection experiments.

A BglII restriction site was incorporated into primer 1 so that ligation of the BglII-digested GlcCerase PCR product into the compatible BamHI site of the pEF6/V5-HisA™ vector eliminated the BamHI restriction site within the multiple cloning site and this modified expression vector will be referred to as pEF6' hereafter. The elimination of this BamHI site within pEF6/V5-HisA™ was necessary so that a unique BamHI site within the GlcCerase cDNA can be utilized for inserting DNA fragments with specific nucleotide substitutions to generate modified GlcCerase enzymes.

To generate GlcCerase-F316A/L317F (designated as pHD105), a GlcCerase minigene containing these amino acid substitutions was synthesized by Integrated DNA Technologies™ between natural flanking 5' BsrGI and 3' BamHI restriction sites. The synthetic modified GlcCerase DNA fragment (~0.5 kb) was released from the pIDTSMART™ plasmid by BsrGI and BamHI restriction digest and subsequently isolated by preparative 1% agarose gel and ligated in-frame into pHD101.4 that had been previously digested with BsrGI and BamHI and dephosphorylated. One microliter of this ligation reaction was used to transform competent E. coli cells and the sample was processed as described above for pHD 101. Miniprep DNA was isolated from individual clones and tested by restriction digest with EcoRI and XbaI. Clone 5 (designated as pHD105.5) was chosen, verified by DNA sequencing and used for further characterization.

To generate GlcCerase-K321N (designated as pHD109), the amino acid substitution was introduced by overlap PCR. Briefly, the N-terminal fragment (~1.1 kb) was generated by using primers A & D and pHD101.4 as the template DNA in PCR reaction 1 while the C-terminal fragment (~0.5 kb) was generated using primers B & C and pHD101.4 template in PCR reaction 2. The entire K321N GlcCerase cDNA was then synthesized in PCR reaction 3 by adding 1 μl from PCR reactions A & B and primers 1 & 2. The resultant PCR product 3 (~1.6 kb) was isolated from a preparative 1% agarose gel as before and digested with EcoRI and NotI restriction endonucleases. PCR product 3 was re-purified and ligated into EcoRI/NotI-digested and dephosphorylated pEF6' vector and processed as described above. Miniprep DNA was isolated from individual clones and tested by restriction digest with EcoRI and XbaI. Clone 3 (designated as pHD109.3) was chosen, verified by DNA sequencing and used for further characterization.

To generate GlcCerase-H145L (designated as pHD110), the amino acid substitution was introduced by overlap PCR. The N-terminal fragment (~0.55 kb) was generated by using primers A & F and pHD101.4 template DNA in PCR reaction 4 while the C-terminal fragment (~1 kb) was generated using primers B & E and pHD101.4 template in PCR reaction 5. The entire H145L GlcCerase cDNA was generated in PCR reaction 6 by adding 1 μl from PCR reactions 4 & 5 and primers A & B. The resultant PCR product 6 (~1.6 kb) was isolated from a preparative 1% agarose gel as before and digested with EcoRI and NotI restriction endonucleases. PCR product 6 was re-purified and ligated into EcoRI/NotI-digested and dephosphorylated pEF6' vector and processed as before. Miniprep DNA was isolated from individual clones and tested by restriction digest with EcoRI and XbaI. Clone 2 (designated as pHD110.2) was chosen, verified by DNA sequencing and used for further characterization.

To generate GlcCerase-H145F (designated as pHD111), the amino acid substitution was introduced by overlap PCR. The N-terminal fragment (~0.55 kb) was generated by using primers A & H and pHD101.4 template DNA in PCR reaction 7 while the C-terminal fragment (~1 kb) was generated using primers B & G and pHD101.4 template in PCR reaction 8. The entire H145L GlcCerase cDNA was generated in PCR reaction 9 by adding 1 μl from PCR reactions 7 & 8 and primers A & B. The resultant PCR product 9 (~1.6 kb) was isolated from a preparative 1% agarose gel as before and digested with EcoRI and NotI restriction endonucleases. PCR product 9 was re-purified and ligated into EcoRI/NotI-digested and dephosphorylated pEF6' vector and processed as before. Miniprep DNA was isolated from individual clones and tested by restriction digest with EcoRI and XbaI. Clone 1 (designated as pHD111.1) was chosen, verified by DNA sequencing and used for further characterization.

To generate GlcCerase-F316A/L317F/K321N (designated as pHD112), the amino acid substitution was introduced into pHD105.5 by overlap PCR. The N-terminal fragment (~1.1 kb) was generated by using primers A & D and pHD105.5 template DNA in PCR reaction 10 while the C-terminal fragment (~0.5 kb) was generated using primers B & C and pHD105.5 template in PCR reaction 11. The entire F316A/L317F/K321N GlcCerase cDNA was generated in PCR reaction 12 by adding 1 μl from PCR reactions 10 & 11 and primers A & B. The resultant PCR product 12 (~1.6 kb) was isolated from a preparative 1% agarose gel as before and digested with EcoRI and NotI restriction endonucleases. PCR product 12 was re-purified and ligated into EcoRI/NotI-digested and dephosphorylated pEF6' vector as described above. Miniprep DNA was isolated from individual clones and tested by restriction digest using EcoRI and XbaI. Clone 7 (designated as pHD112.7) was chosen, verified by DNA sequencing and used for further characterization.

To generate GlcCerase-H145L/F316A/L317F (designated as pHD113), the amino acid substitution was introduced into pHD105.5 by overlap PCR. The N-terminal fragment (~0.55 kb) was generated by using primers A & F and pHD105.5 template DNA in PCR reaction 13 while the C-terminal fragment (~1 kb) was generated using primers B & E and pHD105.5 template in PCR reaction 14. The entire H145L/F316A/L317F GlcCerase cDNA was generated in PCR reaction 15 by adding 1 μl from PCR reactions 13 & 14 and primers A & B. The resultant PCR product 15 (~1.6 kb) was isolated from a preparative 1% agarose gel as before and digested with EcoRI and NotI restriction endonucleases. PCR product 15 was re-purified and ligated into EcoRI/NotI-digested and dephosphorylated pEF6' vector as previously described.

To generate GlcCerase-H145F/F316A/L317F (designated as pHD114), the amino acid substitution was introduced into pHD105.5 by overlap PCR. The N-terminal fragment (~0.55 kb) was generated by using primers A & H and pHD105.5 template DNA in PCR reaction 16 while the C-terminal fragment (~1 kb) was generated using primers B & G and pHD105.5 template in PCR reaction 17. The entire H145F/F316A/L317F GlcCerase cDNA was generated in PCR reaction 18 by adding 1 µl from PCR reactions 16 & 17 and primers A & B. The resultant PCR product 18 (~1.6 kb) was isolated from a preparative 1% agarose gel as before and digested with EcoRI and NotI restriction endonucleases. PCR product 18 was re-purified and ligated into EcoRI/NotI-digested and dephosphorylated pEF6' vector as previously described.

To generate GlcCerase-H145L/K321N (designated as pHD115), both pHD109.3 and pHD110.2 were digested with B srGI and BamHI restriction enzymes and the ~0.5 kb fragment from pHD 109.3 and the ~6.9 kb fragment from pHD110.2 (after treatment with Antarctic phosphatase) were isolated by preparative 1% agarose gel. The ~0.5 kb fragment from pHD109.3 (containing the K321N amino acid substitution) was then ligated in-frame into plasmid pHD110.2 (contains the H145L modification) and processed as before. Miniprep DNA was isolated from individual clones and tested by restriction digest with EcoRI and XbaI. Clone 5 was chosen, verified by DNA sequencing and used for further characterization.

To generate GlcCerase-H145L/F316A/L317F/K321N (designated as pHD116), both pHD112.7 and pHD110.2 will be digested with B srGI and BamHI restriction enzymes and the ~0.5 kb fragment from pHD112.7 and the ~6.9 kb fragment from pHD110.2 (after treatment with Antarctic Phosphatase™) were isolated by preparative 1% agarose gel. The 0.5 kb fragment from pHD112.7 (containing the F316A/L317F/K321N amino acid substitutions) will be ligated in-frame into plasmid pHD110.2 (contains the H145L modification) and processed as before. Miniprep DNA will be isolated from individual clones and tested by restriction digest with EcoRI and XbaI to identify transformed bacterial strain with the correct GlcCerase-H145L/F316A/L317F/K321A cDNA. The selected DNA construct will be verified by DNA sequencing and will be used for further characterization.

To generate GlcCerase-K321A (designated as pHD117), the amino acid substitution was introduced by overlap PCR. Briefly, the N-terminal fragment (~1.1 kb) was generated by using primers A & J and pHD101.4 as the template DNA in PCR reaction 19 while the C-terminal fragment (~0.5 kb) was generated using primers B & I and pHD 101.4 template in PCR reaction 20. PCR products 19 and 20 were isolated by preparative 1% agarose gel and used to as template DNA to synthesize the entire K321A GlcCerase cDNA fragment in PCR reaction 21 using primers A & B. The resultant PCR product 21 (~1.6 kb) was isolated from a preparative 1% agarose gel as before and digested with EcoRI and NotI restriction endonucleases. PCR product 21 was re-purified and ligated into EcoRI/NotI-digested and dephosphorylated pEF6' vector and processed as described above. Miniprep DNA was isolated from individual clones and tested by restriction digest with EcoRI and XbaI. Clone 1 (designated as pHD117.1) was chosen and used for further characterization.

To generate GlcCerase-K321V (designated as pHD118), the amino acid substitution was introduced by overlap PCR. Briefly, the N-terminal fragment (~1.1 kb) was generated by using primers A & L and pHD101.4 as the template DNA in PCR reaction 22 while the C-terminal fragment (~0.5 kb) was generated using primers B & K and pHD 101.4 template in PCR reaction 23. PCR products 22 and 23 were isolated by preparative 1% agarose gel and used to as template DNA to synthesize the entire K321A GlcCerase cDNA fragment in PCR reaction 24 using primers A & B. The resultant PCR product 24 (~1.6 kb) was isolated from a preparative 1% agarose gel as before and digested with EcoRI and NotI restriction endonucleases. PCR product 24 was re-purified and ligated into EcoRI/NotI-digested and dephosphorylated pEF6' vector and processed as described above. Miniprep DNA was isolated from individual clones and tested by restriction digest with EcoRI and XbaI. Clone 7 (designated as pHD118.7) was chosen and used for further characterization.

To generate GlcCerase-F316A/L317F/K321A (designated as pHD119), the amino acid substitution will be introduced into pHD105.5 by overlap PCR. The N-terminal fragment (~1.1 kb) will be generated by using primers A & J and pHD105.5 template DNA in PCR reaction 25 while the C-terminal fragment (~0.5 kb) will be generated using primers B & I and pHD105.5 template in PCR reaction 26. PCR products 25 and 26 will be isolated by preparative 1% agarose gel and will be used to as template DNA to synthesize the entire F316A/L317F/K321A/K321A GlcCerase cDNA fragment in PCR reaction 27 using primers A & B. The resultant PCR product 27 (~1.6 kb) will be isolated from a preparative 1% agarose gel as before and digested with EcoRI and NotI restriction endonucleases. PCR product 27 will be re-purified and ligated into EcoRI/NotI-digested and dephosphorylated pEF6' vector as described above. Miniprep DNA will be isolated from individual clones and tested by restriction digest using EcoRI and XbaI to identify transformed bacterial strain with the correct GlcCerase-F316A/L317F/K321A cDNA. The selected DNA construct will be verified by DNA sequencing and will be used for further characterization.

To generate GlcCerase-F316A/L317F/K321V (designated as pHD120), the amino acid substitution will be introduced into pHD105.5 by overlap PCR. The N-terminal fragment (~1.1 kb) will be generated by using primers A & L and pHD105.5 template DNA in PCR reaction 28 while the C-terminal fragment (~0.5 kb) will be generated using primers B & K and pHD105.5 template in PCR reaction 29. PCR products 28 and 29 will be isolated by preparative 1% agarose gel and will be used to as template DNA to synthesize the entire F316A/L317F/K321A/K321V GlcCerase cDNA fragment in PCR reaction 30 using primers A & B. The resultant PCR product 30 (~1.6 kb) will be isolated from a preparative 1% agarose gel as before and digested with EcoRI and NotI restriction endonucleases. PCR product 30 will be re-purified and ligated into EcoRI/NotI-digested and dephosphorylated pEF6' vector as described above. Miniprep DNA will be isolated from individual clones and tested by restriction digest using EcoRI and XbaI to identify transformed bacterial strain with the correct GlcCerase-F316A/L317F/K321V cDNA. The selected DNA construct will be verified by DNA sequencing and will be used for further characterization.

To generate GlcCerase-H145L/K321A (designated as pHD121), both pHD117.1 and pHD110.2 will be digested with BsrGI and BamHI restriction enzymes and the ~0.5 kb fragment from pHD117.1 and the ~6.9 kb fragment from pHD110.2 (after treatment with Antarctic Phosphatase™) will be isolated by preparative 1% agarose gel. The ~0.5 kb fragment from pHD117.1 (containing the K321A amino acid substitution) will be ligated in-frame into plasmid pHD110.2

(contains the H145L modification) and processed as before. Miniprep DNA was isolated from individual clones and tested by restriction digest with EcoRI and XbaI to identify transformed bacterial strain with the correct GlcCerase-H145L/K321A cDNA. The selected DNA construct will be verified by DNA sequencing and will be used for further characterization.

To generate GlcCerase-H145L/K321V (designated as pHD122), both pHD118.7 and pHD110.2 will be digested with BsrGI and BamHI restriction enzymes and the ~0.5 kb fragment from pHD118.7 and the ~6.9 kb fragment from pHD110.2 (after treatment with Antarctic phosphatase) will be isolated by preparative 1% agarose gel. The ~0.5 kb fragment from pHD118.7 (containing the K321V amino acid substitution) will be ligated in-frame into plasmid pHD110.2 (contains the H145L modification) and processed as before. Miniprep DNA was isolated from individual clones and tested by restriction digest with EcoRI and XbaI to identify transformed bacterial strain with the correct GlcCerase-H145L/K321V cDNA. The selected DNA construct will be verified by DNA sequencing and will be used for further characterization.

Table 3 summarizes the primer sequences mentioned above for constructing modified GlcCerase enzymes.

TABLE 3

| SEQ ID NO: | Primer | Strand | Oligonucleotide Sequence (5'->3') |
|---|---|---|---|
| 25 | A | + | ggcaagatctgaattcgggatggagttttcaagtccttccagag |
| 26 | B | - | tcgagcggccgcaagctagcttatcactggcgacgccacaggtag |
| 27 | C | + | tccagccaacgccaccctag |
| 28 | D | - | ctagggtggcgttggctgga |
| 29 | E | + | tgatttccagttgttgaacttcagcctc |
| 30 | F | - | gaggctgaagttcaacaactggaaatca |
| 31 | G | + | tgatttccagttgttcaacttcagcctc |
| 32 | H | - | gaggctgaagttgaacaactggaaatca |
| 33 | I | + | tccagccgcagccaccctag |
| 34 | J | - | ctagggtggctgcggctgga |
| 35 | K | + | tccagccgtagccaccctagg |
| 36 | L | - | cctagggtggctacggctgga |

Although the present invention has been described in relation to particular embodiments thereof, many other variations and modifications and other uses is apparent to those skilled in the art. It is preferred, therefore, that the present invention be delineated not by the specific disclosure herein, but only by the appended claims.

SEQUENCES

SEQ ID NO: 1
ARPCIPKSFGYSSVVCVCNATYCDSFDPPTFPALGTFSRYESTRSGRRME

LSMGPIQANHTGTGLLLTLQPEQKFQKVKGFGGAMTDAAALNILALSPPA

QNLLLKSYFSEEGIGYNIIRVPMASCDFSIRTYTYADTPDDFQLHNFSLP

EEDTKLKIPLIHRALQLAQRPVSLLASPWTSPTWLKTNGAVNGKGSLKGQ

PGDIYHQTWARYFVKFLDAYAEHKLQFWAVTAENEPSAGLLSGYPFQCLG

FTPEHQRDFIARDLGPTLANSTHHNVRLLMLDDQRLLLPHWAKVVLTDPE

AAKYVHGIAVHWYLDFLAPAKATLGETHRLFPNTMLFASEACVGSKFWEQ

SVRLGSWDRGMQYSHSIITNLLYHVVGWTDWNLALNPEGGPNWVRNFVDS

PIIVDITKDTFYKQPMFYHLGHFSKFIPEGSQRVGLVASQKNDLDAVALM

HPDGSAVVVVLNRSSKDVPLTIKDPAVGFLETISPGYSIHTYLWRRQ

SEQ ID NO: 2
ARPCIPKSFGYSSVVCVCNATYCDSFDPPTFPALGTFSRYESTRSGRRME

LSMGPIQANHTGTGLLLTLQPEQKFQKVKGFGGAMTDAAALNILALSPPA

QNLLLKSYFSEEGIGYNIIRVPMASCDFSIRTYTYADTPDDFQLHNFSLP

EEDTKLKIPLIHRALQLAQRPVSLLASPWTSPTWLKTNGAVNGKGSLKGQ

PGDIYHQTWARYFVKFLDAYAEHKLQFWAVTAENEPSAGLLSGYPFQCLG

FTPEHQRDFIARDLGPTLANSTHHNVRLLMLDDQRLLLPHWAKVVLTDPE

AAKYVHGIAVHWYLDAFAPAKATLGETHRLFPNTMLFASEACVGSKFWEQ

SVRLGSWDRGMQYSHSIITNLLYHVVGWTDWNLALNPEGGPNWVRNFVDS

PIIVDITKDTFYKQPMFYHLGHFSKFIPEGSQRVGLVASQKNDLDAVALM

HPDGSAVVVVLNRSSKDVPLTIKDPAVGFLETISPGYSIHTYLWRRQ

SEQ ID NO: 3
ARPCIPKSFGYSSVVCVCNATYCDSFDPPTFPALGTFSRYESTRSGRRME

LSMGPIQANHTGTGLLLTLQPEQKFQKVKGFGGAMTDAAALNILALSPPA

QNLLLKSYFSEEGIGYNIIRVPMASCDFSIRTYTYADTPDDFQLHNFSLP

EEDTKLKIPLIHRALQLAQRPVSLLASPWTSPTWLKTNGAVNGKGSLKGQ

PGDIYHQTWARYFVKFLDAYAEHKLQFWAVTAENEPSAGLLSGYPFQCLG

```
FTPEHQRDFIARDLGPTLANSTHHNVRLLMLDDQRLLLPHWAKVVLTDPE

AAKYVHGIAVHWYLDFLAPANATLGETHRLFPNTMLFASEACVGSKFWEQ

SVRLGSWDRGMQYSHSIITNLLYHVVGWTDWNLALNPEGGPNWVRNFVDS

PIIVDITKDTFYKQPMFYHLGHFSKFIPEGSQRVGLVASQKNDLDAVALM

HPDGSAVVVVLNRSSKDVPLTIKDPAVGFLETISPGYSIHTYLWRRQ

SEQ ID NO: 4
ARPCIPKSFGYSSVVCVCNATYCDSFDPPTFPALGTFSRYESTRSGRRME

LSMGPIQANHTGTGLLLTLQPEQKFQKVKGFGGAMTDAAALNILALSPPA

QNLLLKSYFSEEGIGYNIIRVPMASCDFSIRTYTYADTPDDFQLLNFSLP

EEDTKLKIPLIHRALQLAQRPVSLLASPWTSPTWLKTNGAVNGKGSLKGQ

PGDIYHQTWARYFVKFLDAYAEHKLQFWAVTAENEPSAGLLSGYPFQCLG

FTPEHQRDFIARDLGPTLANSTHHNVRLLMLDDQRLLLPHWAKVVLTDPE

AAKYVHGIAVHWYLDFLAPAKATLGETHRLFPNTMLFASEACVGSKFWEQ

SVRLGSWDRGMQYSHSIITNLLYHVVGWTDWNLALNPEGGPNWVRNFVDS

PIIVDITKDTFYKQPMFYHLGHFSKFIPEGSQRVGLVASQKNDLDAVALM

HPDGSAVVVVLNRSSKDVPLTIKDPAVGFLETISPGYSIHTYLWRRQ

SEQ ID NO: 5
ARPCIPKSFGYSSVVCVCNATYCDSFDPPTFPALGTFSRYESTRSGRRME

LSMGPIQANHTGTGLLLTLQPEQKFQKVKGFGGAMTDAAALNILALSPPA

QNLLLKSYFSEEGIGYNIIRVPMASCDFSIRTYTYADTPDDFQLFNFSLP

EEDTKLKIPLIHRALQLAQRPVSLLASPWTSPTWLKTNGAVNGKGSLKGQ

PGDIYHQTWARYFVKFLDAYAEHKLQFWAVTAENEPSAGLLSGYPFQCLG

FTPEHQRDFIARDLGPTLANSTHHNVRLLMLDDQRLLLPHWAKVVLTDPE

AAKYVHGIAVHWYLDFLAPAKATLGETHRLFPNTMLFASEACVGSKFWEQ

SVRLGSWDRGMQYSHSIITNLLYHVVGWTDWNLALNPEGGPNWVRNFVDS

PIIVDITKDTFYKQPMFYHLGHFSKFIPEGSQRVGLVASQKNDLDAVALM

HPDGSAVVVVLNRSSKDVPLTIKDPAVGFLETISPGYSIHTYLWRRQ

SEQ ID NO: 6
ARPCIPKSFGYSSVVCVCNATYCDSFDPPTFPALGTFSRYESTRSGRRME

LSMGPIQANHTGTGLLLTLQPEQKFQKVKGFGGAMTDAAALNILALSPPA

QNLLLKSYFSEEGIGYNIIRVPMASCDFSIRTYTYADTPDDFQLHNFSLP

EEDTKLKIPLIHRALQLAQRPVSLLASPWTSPTWLKTNGAVNGKGSLKGQ

PGDIYHQTWARYFVKFLDAYAEHKLQFWAVTAENEPSAGLLSGYPFQCLG

FTPEHQRDFIARDLGPTLANSTHHNVRLLMLDDQRLLLPHWAKVVLTDPE

AAKYVHGIAVHWYLDAFAPANATLGETHRLFPNTMLFASEACVGSKFWEQ

SVRLGSWDRGMQYSHSIITNLLYHVVGWTDWNLALNPEGGPNWVRNFVDS

PIIVDITKDTFYKQPMFYHLGHFSKFIPEGSQRVGLVASQKNDLDAVALM

HPDGSAVVVVLNRSSKDVPLTIKDPAVGFLETISPGYSIHTYLWRRQ

SEQ ID NO: 7
ARPCIPKSFGYSSVVCVCNATYCDSFDPPTFPALGTFSRYESTRSGRRME

LSMGPIQANHTGTGLLLTLQPEQKFQKVKGFGGAMTDAAALNILALSPPA

QNLLLKSYFSEEGIGYNIIRVPMASCDFSIRTYTYADTPDDFQLLNFSLP

EEDTKLKIPLIHRALQLAQRPVSLLASPWTSPTWLKTNGAVNGKGSLKGQ

PGDIYHQTWARYFVKFLDAYAEHKLQFWAVTAENEPSAGLLSGYPFQCLG

FTPEHQRDFIARDLGPTLANSTHHNVRLLMLDDQRLLLPHWAKVVLTDPE

AAKYVHGIAVHWYLDAFAPAKATLGETHRLFPNTMLFASEACVGSKFWEQ

SVRLGSWDRGMQYSHSIITNLLYHVVGWTDWNLALNPEGGPNWVRNFVDS

PIIVDITKDTFYKQPMFYHLGHFSKFIPEGSQRVGLVASQKNDLDAVALM

HPDGSAVVVVLNRSSKDVPLTIKDPAVGFLETISPGYSIHTYLWRRQ

SEQ ID NO: 8
ARPCIPKSFGYSSVVCVCNATYCDSFDPPTFPALGTFSRYESTRSGRRME

LSMGPIQANHTGTGLLLTLQPEQKFQKVKGFGGAMTDAAALNILALSPPA

QNLLLKSYFSEEGIGYNIIRVPMASCDFSIRTYTYADTPDDFQLFNFSLP

EEDTKLKIPLIHRALQLAQRPVSLLASPWTSPTWLKTNGAVNGKGSLKGQ

PGDIYHQTWARYFVKFLDAYAEHKLQFWAVTAENEPSAGLLSGYPFQCLG

FTPEHQRDFIARDLGPTLANSTHHNVRLLMLDDQRLLLPHWAKVVLTDPE

AAKYVHGIAVHWYLDAFAPAKATLGETHRLFPNTMLFASEACVGSKFWEQ

SVRLGSWDRGMQYSHSIITNLLYHVVGWTDWNLALNPEGGPNWVRNFVDS

PIIVDITKDTFYKQPMFYHLGHFSKFIPEGSQRVGLVASQKNDLDAVALM

HPDGSAVVVVLNRSSKDVPLTIKDPAVGFLETISPGYSIHTYLWRRQ

SEQ ID NO: 9
ARPCIPKSFGYSSVVCVCNATYCDSFDPPTFPALGTFSRYESTRSGRRME

LSMGPIQANHTGTGLLLTLQPEQKFQKVKGFGGAMTDAAALNILALSPPA

QNLLLKSYFSEEGIGYNIIRVPMASCDFSIRTYTYADTPDDFQLLNFSLP

EEDTKLKIPLIHRALQLAQRPVSLLASPWTSPTWLKTNGAVNGKGSLKGQ

PGDIYHQTWARYFVKFLDAYAEHKLQFWAVTAENEPSAGLLSGYPFQCLG

FTPEHQRDFIARDLGPTLANSTHHNVRLLMLDDQRLLLPHWAKVVLTDPE

AAKYVHGIAVHWYLDFLAPANATLGETHRLFPNTMLFASEACVGSKFWEQ

SVRLGSWDRGMQYSHSIITNLLYHVVGWTDWNLALNPEGGPNWVRNFVDS

PIIVDITKDTFYKQPMFYHLGHFSKFIPEGSQRVGLVASQKNDLDAVALM

HPDGSAVVVVLNRSSKDVPLTIKDPAVGFLETISPGYSIHTYLWRRQ

SEQ ID NO: 10
ARPCIPKSFGYSSVVCVCNATYCDSFDPPTFPALGTFSRYESTRSGRRME

LSMGPIQANHTGTGLLLTLQPEQKFQKVKGFGGAMTDAAALNILALSPPA

QNLLLKSYFSEEGIGYNIIRVPMASCDFSIRTYTYADTPDDFQLLNFSLP

EEDTKLKIPLIHRALQLAQRPVSLLASPWTSPTWLKTNGAVNGKGSLKGQ

PGDIYHQTWARYFVKFLDAYAEHKLQFWAVTAENEPSAGLLSGYPFQCLG

FTPEHQRDFIARDLGPTLANSTHHNVRLLMLDDQRLLLPHWAKVVLTDPE

AAKYVHGIAVHWYLDAFAPANATLGETHRLFPNTMLFASEACVGSKFWEQ

SVRLGSWDRGMQYSHSIITNLLYHVVGWTDWNLALNPEGGPNWVRNFVDS

PIIVDITKDTFYKQPMFYHLGHFSKFIPEGSQRVGLVASQKNDLDAVALM

HPDGSAVVVVLNRSSKDVPLTIKDPAVGFLETISPGYSIHTYLWRRQ

SEQ ID NO: 11
ARPCIPKSFGYSSVVCVCNATYCDSFDPPTFPALGTFSRYESTRSGRRME

LSMGPIQANHTGTGLLLTLQPEQKFQKVKGFGGAMTDAAALNILALSPPA
```

QNLLLKSYFSEEGIGYNIIRVPMASCDFSIRTYTYADTPDDFQLHNFSLP

EEDTKLKIPLIHRALQLAQRPVSLLASPWTSPTWLKTNGAVNGKGSLKGQ

PGDIYHQTWARYFVKFLDAYAEHKLQFWAVTAENEPSAGLLSGYPFQCLG

FTPEHQRDFIARDLGPTLANSTHHNVRLLMLDDQRLLLPHWAKVVLTDPE

AAKYVHGIAVHWYLDFLAPAAATLGETHRLFPNTMLFASEACVGSKFWEQ

SVRLGSWDRGMQYSHSIITNLLYHVVGWTDWNLALNPEGGPNWVRNFVDS

PIIVDITKDTFYKQPMFYHLGHFSKFIPEGSQRVGLVASQKNDLDAVALM

HPDGSAVVVVLNRSSKDVPLTIKDPAVGFLETISPGYSIHTYLWRRQ

SEQ ID NO: 12
ARPCIPKSFGYSSVVCVCNATYCDSFDPPTFPALGTFSRYESTRSGRRME

LSMGPIQANHTGTGLLLTLQPEQKFQKVKGFGGAMTDAAALNILALSPPA

QNLLLKSYFSEEGIGYNIIRVPMASCDFSIRTYTYADTPDDFQLHNFSLP

EEDTKLKIPLIHRALQLAQRPVSLLASPWTSPTWLKTNGAVNGKGSLKGQ

PGDIYHQTWARYFVKFLDAYAEHKLQFWAVTAENEPSAGLLSGYPFQCLG

FTPEHQRDFIARDLGPTLANSTHHNVRLLMLDDQRLLLPHWAKVVLTDPE

AAKYVHGIAVHWYLDFLAPAVATLGETHRLFPNTMLFASEACVGSKFWEQ

SVRLGSWDRGMQYSHSIITNLLYHVVGWTDWNLALNPEGGPNWVRNFVDS

PIIVDITKDTFYKQPMFYHLGHFSKFIPEGSQRVGLVASQKNDLDAVALM

HPDGSAVVVVLNRSSKDVPLTIKDPAVGFLETISPGYSIHTYLWRRQ

SEQ ID NO: 13
ARPCIPKSFGYSSVVCVCNATYCDSFDPPTFPALGTFSRYESTRSGRRME

LSMGPIQANHTGTGLLLTLQPEQKFQKVKGFGGAMTDAAALNILALSPPA

QNLLLKSYFSEEGIGYNIIRVPMASCDFSIRTYTYADTPDDFQLHNFSLP

EEDTKLKIPLIHRALQLAQRPVSLLASPWTSPTWLKTNGAVNGKGSLKGQ

PGDIYHQTWARYFVKFLDAYAEHKLQFWAVTAENEPSAGLLSGYPFQCLG

FTPEHQRDFIARDLGPTLANSTHHNVRLLMLDDQRLLLPHWAKVVLTDPE

AAKYVHGIAVHWYLDAFAPAAATLGETHRLFPNTMLFASEACVGSKFWEQ

SVRLGSWDRGMQYSHSIITNLLYHVVGWTDWNLALNPEGGPNWVRNFVDS

PIIVDITKDTFYKQPMFYHLGHFSKFIPEGSQRVGLVASQKNDLDAVALM

HPDGSAVVVVLNRSSKDVPLTIKDPAVGFLETISPGYSIHTYLWRRQ

SEQ ID NO: 14
ARPCIPKSFGYSSVVCVCNATYCDSFDPPTFPALGTFSRYESTRSGRRME

LSMGPIQANHTGTGLLLTLQPEQKFQKVKGFGGAMTDAAALNILALSPPA

QNLLLKSYFSEEGIGYNIIRVPMASCDFSIRTYTYADTPDDFQLHNFSLP

EEDTKLKIPLIHRALQLAQRPVSLLASPWTSPTWLKTNGAVNGKGSLKGQ

PGDIYHQTWARYFVKFLDAYAEHKLQFWAVTAENEPSAGLLSGYPFQCLG

FTPEHQRDFIARDLGPTLANSTHHNVRLLMLDDQRLLLPHWAKVVLTDPE

AAKYVHGIAVHWYLDAFAPAVATLGETHRLFPNTMLFASEACVGSKFWEQ

SVRLGSWDRGMQYSHSIITNLLYHVVGWTDWNLALNPEGGPNWVRNFVDS

PIIVDITKDTFYKQPMFYHLGHFSKFIPEGSQRVGLVASQKNDLDAVALM

HPDGSAVVVVLNRSSKDVPLTIKDPAVGFLETISPGYSIHTYLWRRQ

SEQ ID NO: 15
ARPCIPKSFGYSSVVCVCNATYCDSFDPPTFPALGTFSRYESTRSGRRME

LSMGPIQANHTGTGLLLTLQPEQKFQKVKGFGGAMTDAAALNILALSPPA

QNLLLKSYFSEEGIGYNIIRVPMASCDFSIRTYTYADTPDDFQLLNFSLP

EEDTKLKIPLIHRALQLAQRPVSLLASPWTSPTWLKTNGAVNGKGSLKGQ

PGDIYHQTWARYFVKFLDAYAEHKLQFWAVTAENEPSAGLLSGYPFQCLG

FTPEHQRDFIARDLGPTLANSTHHNVRLLMLDDQRLLLPHWAKVVLTDPE

AAKYVHGIAVHWYLDFLAPAAATLGETHRLFPNTMLFASEACVGSKFWEQ

SVRLGSWDRGMQYSHSIITNLLYHVVGWTDWNLALNPEGGPNWVRNFVDS

PIIVDITKDTFYKQPMFYHLGHFSKFIPEGSQRVGLVASQKNDLDAVALM

HPDGSAVVVVLNRSSKDVPLTIKDPAVGFLETISPGYSIHTYLWRRQ

SEQ ID NO: 16
ARPCIPKSFGYSSVVCVCNATYCDSFDPPTFPALGTFSRYESTRSGRRME

LSMGPIQANHTGTGLLLTLQPEQKFQKVKGFGGAMTDAAALNILALSPPA

QNLLLKSYFSEEGIGYNIIRVPMASCDFSIRTYTYADTPDDFQLLNFSLP

EEDTKLKIPLIHRALQLAQRPVSLLASPWTSPTWLKTNGAVNGKGSLKGQ

PGDIYHQTWARYFVKFLDAYAEHKLQFWAVTAENEPSAGLLSGYPFQCLG

FTPEHQRDFIARDLGPTLANSTHHNVRLLMLDDQRLLLPHWAKVVLTDPE

AAKYVHGIAVHWYLDFLAPAVATLGETHRLFPNTMLFASEACVGSKFWEQ

SVRLGSWDRGMQYSHSIITNLLYHVVGWTDWNLALNPEGGPNWVRNFVDS

PIIVDITKDTFYKQPMFYHLGHFSKFIPEGSQRVGLVASQKNDLDAVALM

HPDGSAVVVVLNRSSKDVPLTIKDPAVGFLETISPGYSIHTYLWRRQ

---

What is claimed:

1. A composition comprising:
a variant, recombinant human β-glucocerebrosidase protein, wherein the protein has at least one substitution relative to SEQ ID NO: 1, and wherein the substitution is selected from the group consisting of
F316A relative to SEQ ID NO: 21,
L317F relative to SEQ ID NO: 21,
K321V relative to SEQ ID NO: 21,
K321A relative to SEQ ID NO: 21,
H145L relative to SEQ ID NO: 17,
H145F relative to SEQ ID NO: 17,
and combinations thereof; and
isofagomine.

2. The composition of claim 1, wherein the protein has increased stability relative to human wild-type, recombinant β-glucocerebrosidase.

3. The composition of claim 1, wherein the substitution is selected from the group consisting of F316A, L317F, K321V, K321A, and combinations thereof relative to SEQ ID NO: 21.

4. The composition of claim 1, wherein the substitution is selected from the group consisting of H145L and H145F relative to SEQ ID NO: 17.

5. The composition of claim 1, wherein the protein retains more catalytic activity relative to human wild-type, recombinant β-glucocerebrosidase.

6. The composition of claim 1, wherein catalytic activity is retained at conditions of about neutral pH and about 37° C.

7. The composition of claim 1, wherein the composition has a pH of about 7.5.

8. A method for treating a lysosomal storage disease, comprising administering to a human subject in need thereof the composition of claim 1.

9. The method of claim 8, wherein the lysosomal storage disease is Gaucher disease.

10. A variant, recombinant human β-glucocerebrosidase protein, wherein the protein has a variation relative to SEQ ID NO: 1, the variation consisting essentially of a substitution at a position selected from the group consisting of 316, 317, 321, 145, and combinations thereof.

11. The protein of claim 10, wherein the protein has increased stability relative to human wild-type, recombinant β-glucocerebrosidase.

12. The protein of claim 11, wherein the increased stability is monitored at conditions of about neutral pH and about 37° C. over a period of about three hours.

13. The protein of claim 10, wherein the position is 316, 317 or 321.

14. The protein of claim 10, wherein the position is 145.

15. A composition comprising the protein of claim 10 and isofagomine.

16. A method for treating a lysosomal storage disease, comprising administering to a human subject in need thereof the protein of claim 10.

17. The method of claim 16, wherein the lysosomal storage disease is Gaucher disease.

18. A method for treating a lysosomal storage disease, comprising administering to a human subject in need thereof the composition of claim 15.

19. The method of claim 18, wherein the lysosomal storage disease is Gaucher disease.

20. A composition comprising:
isofagomine; and
a variant, recombinant β-glucocerebrosidase protein characterized as having any one of the following amino acid sequences: SEQ ID NO: 2, SEQ ID NO: 4, SEQ ID NO: 5, SEQ ID NO: 6, SEQ ID NO: 7, SEQ ID NO: 8, SEQ ID NO:9, SEQ ID NO: 10, SEQ ID NO: 11, SEQ ID NO: 12, SEQ ID NO: 13, SEQ ID NO: 14, SEQ ID NO: 15, and SEQ ID NO: 16.

* * * * *

SEQUENCE LISTING

```
<160> NUMBER OF SEQ ID NOS: 36

<210> SEQ ID NO 1
<211> LENGTH: 497
<212> TYPE: PRT
<213> ORGANISM: Artificial Sequence
<220> FEATURE:
<223> OTHER INFORMATION: Human source organism, but with engineered
      mutation

<400> SEQUENCE: 1

Ala Arg Pro Cys Ile Pro Lys Ser Phe Gly Tyr Ser Ser Val Val Cys
1               5                   10                  15
```

```
Val Cys Asn Ala Thr Tyr Cys Asp Ser Phe Asp Pro Thr Phe Pro
            20                  25                  30

Ala Leu Gly Thr Phe Ser Arg Tyr Glu Ser Thr Arg Ser Gly Arg Arg
        35                  40                  45

Met Glu Leu Ser Met Gly Pro Ile Gln Ala Asn His Thr Gly Thr Gly
50                  55                  60

Leu Leu Leu Thr Leu Gln Pro Glu Gln Lys Phe Gln Lys Val Lys Gly
65                  70                  75                  80

Phe Gly Gly Ala Met Thr Asp Ala Ala Leu Asn Ile Leu Ala Leu
                85                  90                  95

Ser Pro Pro Ala Gln Asn Leu Leu Lys Ser Tyr Phe Ser Glu Glu
            100                 105                 110

Gly Ile Gly Tyr Asn Ile Ile Arg Val Pro Met Ala Ser Cys Asp Phe
            115                 120                 125

Ser Ile Arg Thr Tyr Thr Tyr Ala Asp Thr Pro Asp Asp Phe Gln Leu
            130                 135                 140

His Asn Phe Ser Leu Pro Glu Glu Asp Thr Lys Leu Lys Ile Pro Leu
145                 150                 155                 160

Ile His Arg Ala Leu Gln Leu Ala Gln Arg Pro Val Ser Leu Leu Ala
                165                 170                 175

Ser Pro Trp Thr Ser Pro Thr Trp Leu Lys Thr Asn Gly Ala Val Asn
            180                 185                 190

Gly Lys Gly Ser Leu Lys Gly Gln Pro Gly Asp Ile Tyr His Gln Thr
            195                 200                 205

Trp Ala Arg Tyr Phe Val Lys Phe Leu Asp Ala Tyr Ala Glu His Lys
            210                 215                 220

Leu Gln Phe Trp Ala Val Thr Ala Glu Asn Glu Pro Ser Ala Gly Leu
225                 230                 235                 240

Leu Ser Gly Tyr Pro Phe Gln Cys Leu Gly Phe Thr Pro Glu His Gln
                245                 250                 255

Arg Asp Phe Ile Ala Arg Asp Leu Gly Pro Thr Leu Ala Asn Ser Thr
            260                 265                 270

His His Asn Val Arg Leu Leu Met Leu Asp Asp Gln Arg Leu Leu Leu
            275                 280                 285

Pro His Trp Ala Lys Val Val Leu Thr Asp Pro Glu Ala Ala Lys Tyr
            290                 295                 300

Val His Gly Ile Ala Val His Trp Tyr Leu Asp Phe Leu Ala Pro Ala
305                 310                 315                 320

Lys Ala Thr Leu Gly Glu Thr His Arg Leu Phe Pro Asn Thr Met Leu
                325                 330                 335

Phe Ala Ser Glu Ala Cys Val Gly Ser Lys Phe Trp Glu Gln Ser Val
            340                 345                 350

Arg Leu Gly Ser Trp Asp Arg Gly Met Gln Tyr Ser His Ser Ile Ile
            355                 360                 365

Thr Asn Leu Leu Tyr His Val Val Gly Trp Thr Asp Trp Asn Leu Ala
            370                 375                 380

Leu Asn Pro Glu Gly Gly Pro Asn Trp Val Arg Asn Phe Val Asp Ser
385                 390                 395                 400

Pro Ile Ile Val Asp Ile Thr Lys Asp Thr Phe Tyr Lys Gln Pro Met
                405                 410                 415

Phe Tyr His Leu Gly His Phe Ser Lys Phe Ile Pro Glu Gly Ser Gln
            420                 425                 430
```

Arg Val Gly Leu Val Ala Ser Gln Lys Asn Asp Leu Asp Ala Val Ala
            435                 440                 445

Leu Met His Pro Asp Gly Ser Ala Val Val Val Leu Asn Arg Ser
    450                 455                 460

Ser Lys Asp Val Pro Leu Thr Ile Lys Asp Pro Ala Val Gly Phe Leu
465                 470                 475                 480

Glu Thr Ile Ser Pro Gly Tyr Ser Ile His Thr Tyr Leu Trp Arg Arg
                485                 490                 495

Gln

<210> SEQ ID NO 2
<211> LENGTH: 497
<212> TYPE: PRT
<213> ORGANISM: Artificial Sequence
<220> FEATURE:
<223> OTHER INFORMATION: Human source organism, but with engineered
      mutation

<400> SEQUENCE: 2

Ala Arg Pro Cys Ile Pro Lys Ser Phe Gly Tyr Ser Ser Val Val Cys
1               5                   10                  15

Val Cys Asn Ala Thr Tyr Cys Asp Ser Phe Asp Pro Thr Phe Pro
            20                  25                  30

Ala Leu Gly Thr Phe Ser Arg Tyr Glu Ser Thr Arg Ser Gly Arg Arg
            35                  40                  45

Met Glu Leu Ser Met Gly Pro Ile Gln Ala Asn His Thr Gly Thr Gly
    50                  55                  60

Leu Leu Leu Thr Leu Gln Pro Glu Gln Lys Phe Gln Lys Val Lys Gly
65                  70                  75                  80

Phe Gly Gly Ala Met Thr Asp Ala Ala Ala Leu Asn Ile Leu Ala Leu
                85                  90                  95

Ser Pro Pro Ala Gln Asn Leu Leu Leu Lys Ser Tyr Phe Ser Glu Glu
            100                 105                 110

Gly Ile Gly Tyr Asn Ile Ile Arg Val Pro Met Ala Ser Cys Asp Phe
        115                 120                 125

Ser Ile Arg Thr Tyr Thr Tyr Ala Asp Thr Pro Asp Asp Phe Gln Leu
    130                 135                 140

His Asn Phe Ser Leu Pro Glu Glu Asp Thr Lys Leu Lys Ile Pro Leu
145                 150                 155                 160

Ile His Arg Ala Leu Gln Leu Ala Gln Arg Pro Val Ser Leu Leu Ala
                165                 170                 175

Ser Pro Trp Thr Ser Pro Thr Trp Leu Lys Thr Asn Gly Ala Val Asn
            180                 185                 190

Gly Lys Gly Ser Leu Lys Gly Gln Pro Gly Asp Ile Tyr His Gln Thr
        195                 200                 205

Trp Ala Arg Tyr Phe Val Lys Phe Leu Asp Ala Tyr Ala Glu His Lys
    210                 215                 220

Leu Gln Phe Trp Ala Val Thr Ala Glu Asn Glu Pro Ser Ala Gly Leu
225                 230                 235                 240

Leu Ser Gly Tyr Pro Phe Gln Cys Leu Gly Phe Thr Pro Glu His Gln
                245                 250                 255

Arg Asp Phe Ile Ala Arg Asp Leu Gly Pro Thr Leu Ala Asn Ser Thr
            260                 265                 270

His His Asn Val Arg Leu Leu Met Leu Asp Asp Gln Arg Leu Leu Leu
        275                 280                 285

```
Pro His Trp Ala Lys Val Val Leu Thr Asp Pro Glu Ala Ala Lys Tyr
290                 295                 300

Val His Gly Ile Ala Val His Trp Tyr Leu Asp Ala Phe Ala Pro Ala
305                 310                 315                 320

Lys Ala Thr Leu Gly Glu Thr His Arg Leu Phe Pro Asn Thr Met Leu
                325                 330                 335

Phe Ala Ser Glu Ala Cys Val Gly Ser Lys Phe Trp Glu Gln Ser Val
                340                 345                 350

Arg Leu Gly Ser Trp Asp Arg Gly Met Gln Tyr Ser His Ser Ile Ile
                355                 360                 365

Thr Asn Leu Leu Tyr His Val Val Gly Trp Thr Asp Trp Asn Leu Ala
370                 375                 380

Leu Asn Pro Glu Gly Gly Pro Asn Trp Val Arg Asn Phe Val Asp Ser
385                 390                 395                 400

Pro Ile Ile Val Asp Ile Thr Lys Asp Thr Phe Tyr Lys Gln Pro Met
                405                 410                 415

Phe Tyr His Leu Gly His Phe Ser Lys Phe Ile Pro Glu Gly Ser Gln
                420                 425                 430

Arg Val Gly Leu Val Ala Ser Gln Lys Asn Asp Leu Asp Ala Val Ala
                435                 440                 445

Leu Met His Pro Asp Gly Ser Ala Val Val Val Leu Asn Arg Ser
450                 455                 460

Ser Lys Asp Val Pro Leu Thr Ile Lys Asp Pro Ala Val Gly Phe Leu
465                 470                 475                 480

Glu Thr Ile Ser Pro Gly Tyr Ser Ile His Thr Tyr Leu Trp Arg Arg
                485                 490                 495

Gln

<210> SEQ ID NO 3
<211> LENGTH: 497
<212> TYPE: PRT
<213> ORGANISM: Artificial Sequence
<220> FEATURE:
<223> OTHER INFORMATION: Human source organism, but with engineered
      mutation

<400> SEQUENCE: 3

Ala Arg Pro Cys Ile Pro Lys Ser Phe Gly Tyr Ser Ser Val Val Cys
1               5                   10                  15

Val Cys Asn Ala Thr Tyr Cys Asp Ser Phe Asp Pro Thr Phe Pro
            20                  25                  30

Ala Leu Gly Thr Phe Ser Arg Tyr Glu Ser Thr Arg Ser Gly Arg Arg
                35                  40                  45

Met Glu Leu Ser Met Gly Pro Ile Gln Ala Asn His Thr Gly Thr Gly
            50                  55                  60

Leu Leu Leu Thr Leu Gln Pro Glu Gln Lys Phe Gln Lys Val Lys Gly
65                  70                  75                  80

Phe Gly Gly Ala Met Thr Asp Ala Ala Ala Leu Asn Ile Leu Ala Leu
                85                  90                  95

Ser Pro Pro Ala Gln Asn Leu Leu Leu Lys Ser Tyr Phe Ser Glu Glu
                100                 105                 110

Gly Ile Gly Tyr Asn Ile Ile Arg Val Pro Met Ala Ser Cys Asp Phe
            115                 120                 125

Ser Ile Arg Thr Tyr Thr Tyr Ala Asp Thr Pro Asp Asp Phe Gln Leu
    130                 135                 140
```

His Asn Phe Ser Leu Pro Glu Glu Asp Thr Lys Leu Lys Ile Pro Leu
145                 150                 155                 160

Ile His Arg Ala Leu Gln Leu Ala Gln Arg Pro Val Ser Leu Leu Ala
            165                 170                 175

Ser Pro Trp Thr Ser Pro Thr Trp Leu Lys Thr Asn Gly Ala Val Asn
        180                 185                 190

Gly Lys Gly Ser Leu Lys Gly Gln Pro Gly Asp Ile Tyr His Gln Thr
    195                 200                 205

Trp Ala Arg Tyr Phe Val Lys Phe Leu Asp Ala Tyr Ala Glu His Lys
210                 215                 220

Leu Gln Phe Trp Ala Val Thr Ala Glu Asn Glu Pro Ser Ala Gly Leu
225                 230                 235                 240

Leu Ser Gly Tyr Pro Phe Gln Cys Leu Gly Phe Thr Pro Glu His Gln
                245                 250                 255

Arg Asp Phe Ile Ala Arg Asp Leu Gly Pro Thr Leu Ala Asn Ser Thr
            260                 265                 270

His His Asn Val Arg Leu Leu Met Leu Asp Asp Gln Arg Leu Leu Leu
        275                 280                 285

Pro His Trp Ala Lys Val Val Leu Thr Asp Pro Glu Ala Ala Lys Tyr
    290                 295                 300

Val His Gly Ile Ala Val His Trp Tyr Leu Asp Phe Leu Ala Pro Ala
305                 310                 315                 320

Asn Ala Thr Leu Gly Glu Thr His Arg Leu Phe Pro Asn Thr Met Leu
                325                 330                 335

Phe Ala Ser Glu Ala Cys Val Gly Ser Lys Phe Trp Glu Gln Ser Val
            340                 345                 350

Arg Leu Gly Ser Trp Asp Arg Gly Met Gln Tyr Ser His Ser Ile Ile
        355                 360                 365

Thr Asn Leu Leu Tyr His Val Val Gly Trp Thr Asp Trp Asn Leu Ala
    370                 375                 380

Leu Asn Pro Glu Gly Gly Pro Asn Trp Val Arg Asn Phe Val Asp Ser
385                 390                 395                 400

Pro Ile Ile Val Asp Ile Thr Lys Asp Thr Phe Tyr Lys Gln Pro Met
                405                 410                 415

Phe Tyr His Leu Gly His Phe Ser Lys Phe Ile Pro Glu Gly Ser Gln
            420                 425                 430

Arg Val Gly Leu Val Ala Ser Gln Lys Asn Asp Leu Asp Ala Val Ala
        435                 440                 445

Leu Met His Pro Asp Gly Ser Ala Val Val Val Leu Asn Arg Ser
    450                 455                 460

Ser Lys Asp Val Pro Leu Thr Ile Lys Asp Pro Ala Val Gly Phe Leu
465                 470                 475                 480

Glu Thr Ile Ser Pro Gly Tyr Ser Ile His Thr Tyr Leu Trp Arg Arg
                485                 490                 495

Gln

<210> SEQ ID NO 4
<211> LENGTH: 497
<212> TYPE: PRT
<213> ORGANISM: Artificial Sequence
<220> FEATURE:
<223> OTHER INFORMATION: Human source organism, but with engineered
      mutation

<400> SEQUENCE: 4

-continued

```
Ala Arg Pro Cys Ile Pro Lys Ser Phe Gly Tyr Ser Val Val Cys
1               5                   10                  15

Val Cys Asn Ala Thr Tyr Cys Asp Ser Phe Asp Pro Thr Phe Pro
            20                  25                  30

Ala Leu Gly Thr Phe Ser Arg Tyr Glu Ser Thr Arg Ser Gly Arg Arg
            35                  40                  45

Met Glu Leu Ser Met Gly Pro Ile Gln Ala Asn His Thr Gly Thr Gly
        50                  55                  60

Leu Leu Leu Thr Leu Gln Pro Glu Gln Lys Phe Gln Lys Val Lys Gly
65                  70                  75                  80

Phe Gly Gly Ala Met Thr Asp Ala Ala Ala Leu Asn Ile Leu Ala Leu
                85                  90                  95

Ser Pro Pro Ala Gln Asn Leu Leu Lys Ser Tyr Phe Ser Glu Glu
            100                 105                 110

Gly Ile Gly Tyr Asn Ile Ile Arg Val Pro Met Ala Ser Cys Asp Phe
            115                 120                 125

Ser Ile Arg Thr Tyr Thr Tyr Ala Asp Thr Pro Asp Asp Phe Gln Leu
        130                 135                 140

Leu Asn Phe Ser Leu Pro Glu Glu Asp Thr Lys Leu Lys Ile Pro Leu
145                 150                 155                 160

Ile His Arg Ala Leu Gln Leu Ala Gln Arg Pro Val Ser Leu Leu Ala
                165                 170                 175

Ser Pro Trp Thr Ser Pro Thr Trp Leu Lys Thr Asn Gly Ala Val Asn
            180                 185                 190

Gly Lys Gly Ser Leu Lys Gly Gln Pro Gly Asp Ile Tyr His Gln Thr
            195                 200                 205

Trp Ala Arg Tyr Phe Val Lys Phe Leu Asp Ala Tyr Ala Glu His Lys
        210                 215                 220

Leu Gln Phe Trp Ala Val Thr Ala Glu Asn Glu Pro Ser Ala Gly Leu
225                 230                 235                 240

Leu Ser Gly Tyr Pro Phe Gln Cys Leu Gly Phe Thr Pro Glu His Gln
                245                 250                 255

Arg Asp Phe Ile Ala Arg Asp Leu Gly Pro Thr Leu Ala Asn Ser Thr
            260                 265                 270

His His Asn Val Arg Leu Leu Met Leu Asp Asp Gln Arg Leu Leu Leu
        275                 280                 285

Pro His Trp Ala Lys Val Val Leu Thr Asp Pro Glu Ala Ala Lys Tyr
290                 295                 300

Val His Gly Ile Ala Val His Trp Tyr Leu Asp Phe Leu Ala Pro Ala
305                 310                 315                 320

Lys Ala Thr Leu Gly Glu Thr His Arg Leu Phe Pro Asn Thr Met Leu
                325                 330                 335

Phe Ala Ser Glu Ala Cys Val Gly Ser Lys Phe Trp Glu Gln Ser Val
            340                 345                 350

Arg Leu Gly Ser Trp Asp Arg Gly Met Gln Tyr Ser His Ser Ile Ile
        355                 360                 365

Thr Asn Leu Leu Tyr His Val Val Gly Trp Thr Asp Trp Asn Leu Ala
370                 375                 380

Leu Asn Pro Glu Gly Gly Pro Asn Trp Val Arg Asn Phe Val Asp Ser
385                 390                 395                 400

Pro Ile Ile Val Asp Ile Thr Lys Asp Thr Phe Tyr Lys Gln Pro Met
                405                 410                 415

Phe Tyr His Leu Gly His Phe Ser Lys Phe Ile Pro Glu Gly Ser Gln
```

```
                420            425            430
Arg Val Gly Leu Val Ala Ser Gln Lys Asn Asp Leu Asp Ala Val Ala
            435                440                445

Leu Met His Pro Asp Gly Ser Ala Val Val Val Leu Asn Arg Ser
450                455                460

Ser Lys Asp Val Pro Leu Thr Ile Lys Asp Pro Ala Val Gly Phe Leu
465                470                475                480

Glu Thr Ile Ser Pro Gly Tyr Ser Ile His Thr Tyr Leu Trp Arg Arg
            485                490                495

Gln

<210> SEQ ID NO 5
<211> LENGTH: 497
<212> TYPE: PRT
<213> ORGANISM: Artificial Sequence
<220> FEATURE:
<223> OTHER INFORMATION: Human source organism, but with engineered
      mutation

<400> SEQUENCE: 5

Ala Arg Pro Cys Ile Pro Lys Ser Phe Gly Tyr Ser Ser Val Val Cys
1               5                   10                  15

Val Cys Asn Ala Thr Tyr Cys Asp Ser Phe Asp Pro Pro Thr Phe Pro
            20                  25                  30

Ala Leu Gly Thr Phe Ser Arg Tyr Glu Ser Thr Arg Ser Gly Arg Arg
        35                  40                  45

Met Glu Leu Ser Met Gly Pro Ile Gln Ala Asn His Thr Gly Thr Gly
    50                  55                  60

Leu Leu Leu Thr Leu Gln Pro Glu Gln Lys Phe Gln Lys Val Lys Gly
65                  70                  75                  80

Phe Gly Gly Ala Met Thr Asp Ala Ala Ala Leu Asn Ile Leu Ala Leu
                85                  90                  95

Ser Pro Pro Ala Gln Asn Leu Leu Leu Lys Ser Tyr Phe Ser Glu Glu
            100                 105                 110

Gly Ile Gly Tyr Asn Ile Ile Arg Val Pro Met Ala Ser Cys Asp Phe
        115                 120                 125

Ser Ile Arg Thr Tyr Thr Tyr Ala Asp Thr Pro Asp Asp Phe Gln Leu
    130                 135                 140

Phe Asn Phe Ser Leu Pro Glu Glu Asp Thr Lys Leu Lys Ile Pro Leu
145                 150                 155                 160

Ile His Arg Ala Leu Gln Leu Ala Gln Arg Pro Val Ser Leu Leu Ala
                165                 170                 175

Ser Pro Trp Thr Ser Pro Thr Trp Leu Lys Thr Asn Gly Ala Val Asn
            180                 185                 190

Gly Lys Gly Ser Leu Lys Gly Gln Pro Gly Asp Ile Tyr His Gln Thr
        195                 200                 205

Trp Ala Arg Tyr Phe Val Lys Phe Leu Asp Ala Tyr Ala Glu His Lys
    210                 215                 220

Leu Gln Phe Trp Ala Val Thr Ala Glu Asn Glu Pro Ser Ala Gly Leu
225                 230                 235                 240

Leu Ser Gly Tyr Pro Phe Gln Cys Leu Gly Phe Thr Pro Glu His Gln
                245                 250                 255

Arg Asp Phe Ile Ala Arg Asp Leu Gly Pro Thr Leu Ala Asn Ser Thr
            260                 265                 270

His His Asn Val Arg Leu Leu Met Leu Asp Asp Gln Arg Leu Leu Leu
```

```
                       275                 280                 285
Pro His Trp Ala Lys Val Val Leu Thr Asp Pro Glu Ala Ala Lys Tyr
290                 295                 300

Val His Gly Ile Ala Val His Trp Tyr Leu Asp Phe Leu Ala Pro Ala
305                 310                 315                 320

Lys Ala Thr Leu Gly Glu Thr His Arg Leu Phe Pro Asn Thr Met Leu
                325                 330                 335

Phe Ala Ser Glu Ala Cys Val Gly Ser Lys Phe Trp Glu Gln Ser Val
            340                 345                 350

Arg Leu Gly Ser Trp Asp Arg Gly Met Gln Tyr Ser His Ser Ile Ile
        355                 360                 365

Thr Asn Leu Leu Tyr His Val Val Gly Trp Thr Asp Trp Asn Leu Ala
370                 375                 380

Leu Asn Pro Glu Gly Gly Pro Asn Trp Val Arg Asn Phe Val Asp Ser
385                 390                 395                 400

Pro Ile Ile Val Asp Ile Thr Lys Asp Thr Phe Tyr Lys Gln Pro Met
                405                 410                 415

Phe Tyr His Leu Gly His Phe Ser Lys Phe Ile Pro Glu Gly Ser Gln
            420                 425                 430

Arg Val Gly Leu Val Ala Ser Gln Lys Asn Asp Leu Asp Ala Val Ala
        435                 440                 445

Leu Met His Pro Asp Gly Ser Ala Val Val Val Leu Asn Arg Ser
450                 455                 460

Ser Lys Asp Val Pro Leu Thr Ile Lys Asp Pro Ala Val Gly Phe Leu
465                 470                 475                 480

Glu Thr Ile Ser Pro Gly Tyr Ser Ile His Thr Tyr Leu Trp Arg Arg
                485                 490                 495

Gln

<210> SEQ ID NO 6
<211> LENGTH: 497
<212> TYPE: PRT
<213> ORGANISM: Artificial Sequence
<220> FEATURE:
<223> OTHER INFORMATION: Human source organism, but with engineered
      mutation

<400> SEQUENCE: 6

Ala Arg Pro Cys Ile Pro Lys Ser Phe Gly Tyr Ser Ser Val Val Cys
1               5                   10                  15

Val Cys Asn Ala Thr Tyr Cys Asp Ser Phe Asp Pro Pro Thr Phe Pro
                20                  25                  30

Ala Leu Gly Thr Phe Ser Arg Tyr Glu Ser Thr Arg Ser Gly Arg Arg
            35                  40                  45

Met Glu Leu Ser Met Gly Pro Ile Gln Ala Asn His Thr Gly Thr Gly
        50                  55                  60

Leu Leu Leu Thr Leu Gln Pro Glu Gln Lys Phe Gln Lys Val Lys Gly
65                  70                  75                  80

Phe Gly Gly Ala Met Thr Asp Ala Ala Ala Leu Asn Ile Leu Ala Leu
                85                  90                  95

Ser Pro Pro Ala Gln Asn Leu Leu Leu Lys Ser Tyr Phe Ser Glu Glu
                100                 105                 110

Gly Ile Gly Tyr Asn Ile Ile Arg Val Pro Met Ala Ser Cys Asp Phe
            115                 120                 125

Ser Ile Arg Thr Tyr Thr Tyr Ala Asp Thr Pro Asp Asp Phe Gln Leu
```

```
            130                 135                 140
His Asn Phe Ser Leu Pro Glu Glu Asp Thr Lys Leu Lys Ile Pro Leu
145                 150                 155                 160

Ile His Arg Ala Leu Gln Leu Ala Gln Arg Pro Val Ser Leu Leu Ala
                165                 170                 175

Ser Pro Trp Thr Ser Pro Thr Trp Leu Lys Thr Asn Gly Ala Val Asn
            180                 185                 190

Gly Lys Gly Ser Leu Lys Gly Gln Pro Gly Asp Ile Tyr His Gln Thr
        195                 200                 205

Trp Ala Arg Tyr Phe Val Lys Phe Leu Asp Ala Tyr Ala Glu His Lys
    210                 215                 220

Leu Gln Phe Trp Ala Val Thr Ala Glu Asn Glu Pro Ser Ala Gly Leu
225                 230                 235                 240

Leu Ser Gly Tyr Pro Phe Gln Cys Leu Gly Phe Thr Pro Glu His Gln
                245                 250                 255

Arg Asp Phe Ile Ala Arg Asp Leu Gly Pro Thr Leu Ala Asn Ser Thr
            260                 265                 270

His His Asn Val Arg Leu Leu Met Leu Asp Asp Gln Arg Leu Leu Leu
        275                 280                 285

Pro His Trp Ala Lys Val Val Leu Thr Asp Pro Glu Ala Ala Lys Tyr
    290                 295                 300

Val His Gly Ile Ala Val His Trp Tyr Leu Asp Ala Phe Ala Pro Ala
305                 310                 315                 320

Asn Ala Thr Leu Gly Glu Thr His Arg Leu Phe Pro Asn Thr Met Leu
                325                 330                 335

Phe Ala Ser Glu Ala Cys Val Gly Ser Lys Phe Trp Glu Gln Ser Val
            340                 345                 350

Arg Leu Gly Ser Trp Asp Arg Gly Met Gln Tyr Ser His Ser Ile Ile
        355                 360                 365

Thr Asn Leu Leu Tyr His Val Val Gly Trp Thr Asp Trp Asn Leu Ala
    370                 375                 380

Leu Asn Pro Glu Gly Gly Pro Asn Trp Val Arg Asn Phe Val Asp Ser
385                 390                 395                 400

Pro Ile Ile Val Asp Ile Thr Lys Asp Thr Phe Tyr Lys Gln Pro Met
                405                 410                 415

Phe Tyr His Leu Gly His Phe Ser Lys Phe Ile Pro Glu Gly Ser Gln
            420                 425                 430

Arg Val Gly Leu Val Ala Ser Gln Lys Asn Asp Leu Asp Ala Val Ala
        435                 440                 445

Leu Met His Pro Asp Gly Ser Ala Val Val Val Leu Asn Arg Ser
    450                 455                 460

Ser Lys Asp Val Pro Leu Thr Ile Lys Asp Pro Ala Val Gly Phe Leu
465                 470                 475                 480

Glu Thr Ile Ser Pro Gly Tyr Ser Ile His Thr Tyr Leu Trp Arg Arg
                485                 490                 495

Gln

<210> SEQ ID NO 7
<211> LENGTH: 497
<212> TYPE: PRT
<213> ORGANISM: Artificial Sequence
<220> FEATURE:
<223> OTHER INFORMATION: Human source organism, but with engineered
      mutation
```

```
<400> SEQUENCE: 7

Ala Arg Pro Cys Ile Pro Lys Ser Phe Gly Tyr Ser Ser Val Val Cys
1               5                   10                  15

Val Cys Asn Ala Thr Tyr Cys Asp Ser Phe Asp Pro Thr Phe Pro
            20                  25                  30

Ala Leu Gly Thr Phe Ser Arg Tyr Glu Ser Thr Arg Ser Gly Arg Arg
            35                  40                  45

Met Glu Leu Ser Met Gly Pro Ile Gln Ala Asn His Thr Gly Thr Gly
            50                  55                  60

Leu Leu Leu Thr Leu Gln Pro Glu Gln Lys Phe Gln Lys Val Lys Gly
65                  70                  75                  80

Phe Gly Gly Ala Met Thr Asp Ala Ala Leu Asn Ile Leu Ala Leu
                85                  90                  95

Ser Pro Pro Ala Gln Asn Leu Leu Leu Lys Ser Tyr Phe Ser Glu Glu
            100                 105                 110

Gly Ile Gly Tyr Asn Ile Ile Arg Val Pro Met Ala Ser Cys Asp Phe
            115                 120                 125

Ser Ile Arg Thr Tyr Thr Tyr Ala Asp Thr Pro Asp Asp Phe Gln Leu
            130                 135                 140

Leu Asn Phe Ser Leu Pro Glu Glu Asp Thr Lys Leu Lys Ile Pro Leu
145                 150                 155                 160

Ile His Arg Ala Leu Gln Leu Ala Gln Arg Pro Val Ser Leu Leu Ala
                165                 170                 175

Ser Pro Trp Thr Ser Pro Thr Trp Leu Lys Thr Asn Gly Ala Val Asn
            180                 185                 190

Gly Lys Gly Ser Leu Lys Gly Gln Pro Gly Asp Ile Tyr His Gln Thr
            195                 200                 205

Trp Ala Arg Tyr Phe Val Lys Phe Leu Asp Ala Tyr Ala Glu His Lys
210                 215                 220

Leu Gln Phe Trp Ala Val Thr Ala Glu Asn Glu Pro Ser Ala Gly Leu
225                 230                 235                 240

Leu Ser Gly Tyr Pro Phe Gln Cys Leu Gly Phe Thr Pro Glu His Gln
                245                 250                 255

Arg Asp Phe Ile Ala Arg Asp Leu Gly Pro Thr Leu Ala Asn Ser Thr
                260                 265                 270

His His Asn Val Arg Leu Leu Met Leu Asp Asp Gln Arg Leu Leu Leu
            275                 280                 285

Pro His Trp Ala Lys Val Val Leu Thr Asp Pro Glu Ala Ala Lys Tyr
            290                 295                 300

Val His Gly Ile Ala Val His Trp Tyr Leu Asp Ala Phe Ala Pro Ala
305                 310                 315                 320

Lys Ala Thr Leu Gly Glu Thr His Arg Leu Phe Pro Asn Thr Met Leu
                325                 330                 335

Phe Ala Ser Glu Ala Cys Val Gly Ser Lys Phe Trp Glu Gln Ser Val
            340                 345                 350

Arg Leu Gly Ser Trp Asp Arg Gly Met Gln Tyr Ser His Ser Ile Ile
            355                 360                 365

Thr Asn Leu Leu Tyr His Val Val Gly Trp Thr Asp Trp Asn Leu Ala
            370                 375                 380

Leu Asn Pro Glu Gly Gly Pro Asn Trp Val Arg Asn Phe Val Asp Ser
385                 390                 395                 400

Pro Ile Ile Val Asp Ile Thr Lys Asp Thr Phe Tyr Lys Gln Pro Met
                405                 410                 415
```

```
Phe Tyr His Leu Gly His Phe Ser Lys Phe Ile Pro Glu Gly Ser Gln
            420                 425                 430

Arg Val Gly Leu Val Ala Ser Gln Lys Asn Asp Leu Asp Ala Val Ala
                435                 440                 445

Leu Met His Pro Asp Gly Ser Ala Val Val Val Leu Asn Arg Ser
            450                 455                 460

Ser Lys Asp Val Pro Leu Thr Ile Lys Asp Pro Ala Val Gly Phe Leu
465                 470                 475                 480

Glu Thr Ile Ser Pro Gly Tyr Ser Ile His Thr Tyr Leu Trp Arg Arg
                485                 490                 495

Gln

<210> SEQ ID NO 8
<211> LENGTH: 497
<212> TYPE: PRT
<213> ORGANISM: Artificial Sequence
<220> FEATURE:
<223> OTHER INFORMATION: Human source organism, but with engineered
      mutation

<400> SEQUENCE: 8

Ala Arg Pro Cys Ile Pro Lys Ser Phe Gly Tyr Ser Ser Val Val Cys
1               5                   10                  15

Val Cys Asn Ala Thr Tyr Cys Asp Ser Phe Asp Pro Pro Thr Phe Pro
                20                  25                  30

Ala Leu Gly Thr Phe Ser Arg Tyr Glu Ser Thr Arg Ser Gly Arg Arg
            35                  40                  45

Met Glu Leu Ser Met Gly Pro Ile Gln Ala Asn His Thr Gly Thr Gly
        50                  55                  60

Leu Leu Leu Thr Leu Gln Pro Glu Gln Lys Phe Gln Lys Val Lys Gly
65                  70                  75                  80

Phe Gly Gly Ala Met Thr Asp Ala Ala Ala Leu Asn Ile Leu Ala Leu
                85                  90                  95

Ser Pro Pro Ala Gln Asn Leu Leu Leu Lys Ser Tyr Phe Ser Glu Glu
                100                 105                 110

Gly Ile Gly Tyr Asn Ile Ile Arg Val Pro Met Ala Ser Cys Asp Phe
            115                 120                 125

Ser Ile Arg Thr Tyr Thr Tyr Ala Asp Thr Pro Asp Asp Phe Gln Leu
        130                 135                 140

Phe Asn Phe Ser Leu Pro Glu Glu Asp Thr Lys Leu Lys Ile Pro Leu
145                 150                 155                 160

Ile His Arg Ala Leu Gln Leu Ala Gln Arg Pro Val Ser Leu Leu Ala
                165                 170                 175

Ser Pro Trp Thr Ser Pro Thr Trp Leu Lys Thr Asn Gly Ala Val Asn
            180                 185                 190

Gly Lys Gly Ser Leu Lys Gly Gln Pro Gly Asp Ile Tyr His Gln Thr
        195                 200                 205

Trp Ala Arg Tyr Phe Val Lys Phe Leu Asp Ala Tyr Ala Glu His Lys
    210                 215                 220

Leu Gln Phe Trp Ala Val Thr Ala Glu Asn Glu Pro Ser Ala Gly Leu
225                 230                 235                 240

Leu Ser Gly Tyr Pro Phe Gln Cys Leu Gly Phe Thr Pro Glu His Gln
                245                 250                 255

Arg Asp Phe Ile Ala Arg Asp Leu Gly Pro Thr Leu Ala Asn Ser Thr
            260                 265                 270
```

```
His His Asn Val Arg Leu Leu Met Leu Asp Asp Gln Arg Leu Leu Leu
            275                 280                 285

Pro His Trp Ala Lys Val Val Leu Thr Asp Pro Glu Ala Ala Lys Tyr
290                     295                 300

Val His Gly Ile Ala Val His Trp Tyr Leu Asp Ala Phe Ala Pro Ala
305                     310                 315                 320

Lys Ala Thr Leu Gly Glu Thr His Arg Leu Phe Pro Asn Thr Met Leu
                    325                 330                 335

Phe Ala Ser Glu Ala Cys Val Gly Ser Lys Phe Trp Glu Gln Ser Val
                340                 345                 350

Arg Leu Gly Ser Trp Asp Arg Gly Met Gln Tyr Ser His Ser Ile Ile
            355                 360                 365

Thr Asn Leu Leu Tyr His Val Val Gly Trp Thr Asp Trp Asn Leu Ala
        370                 375                 380

Leu Asn Pro Glu Gly Gly Pro Asn Trp Val Arg Asn Phe Val Asp Ser
385                 390                 395                 400

Pro Ile Ile Val Asp Ile Thr Lys Asp Thr Phe Tyr Lys Gln Pro Met
                405                 410                 415

Phe Tyr His Leu Gly His Phe Ser Lys Phe Ile Pro Glu Gly Ser Gln
            420                 425                 430

Arg Val Gly Leu Val Ala Ser Gln Lys Asn Asp Leu Asp Ala Val Ala
        435                 440                 445

Leu Met His Pro Asp Gly Ser Ala Val Val Val Leu Asn Arg Ser
450                 455                 460

Ser Lys Asp Val Pro Leu Thr Ile Lys Asp Pro Ala Val Gly Phe Leu
465                 470                 475                 480

Glu Thr Ile Ser Pro Gly Tyr Ser Ile His Thr Tyr Leu Trp Arg Arg
                485                 490                 495

Gln

<210> SEQ ID NO 9
<211> LENGTH: 497
<212> TYPE: PRT
<213> ORGANISM: Artificial Sequence
<220> FEATURE:
<223> OTHER INFORMATION: Human source organism, but with engineered
      mutation

<400> SEQUENCE: 9

Ala Arg Pro Cys Ile Pro Lys Ser Phe Gly Tyr Ser Ser Val Val Cys
1               5                   10                  15

Val Cys Asn Ala Thr Tyr Cys Asp Ser Phe Asp Pro Thr Phe Pro
            20                  25                  30

Ala Leu Gly Thr Phe Ser Arg Tyr Glu Ser Thr Arg Ser Gly Arg Arg
        35                  40                  45

Met Glu Leu Ser Met Gly Pro Ile Gln Ala Asn His Thr Gly Thr Gly
    50                  55                  60

Leu Leu Leu Thr Leu Gln Pro Glu Gln Lys Phe Gln Lys Val Lys Gly
65                  70                  75                  80

Phe Gly Gly Ala Met Thr Asp Ala Ala Ala Leu Asn Ile Leu Ala Leu
                85                  90                  95

Ser Pro Pro Ala Gln Asn Leu Leu Lys Ser Tyr Phe Ser Glu Glu
            100                 105                 110

Gly Ile Gly Tyr Asn Ile Ile Arg Val Pro Met Ala Ser Cys Asp Phe
        115                 120                 125
```

Ser Ile Arg Thr Tyr Thr Tyr Ala Asp Thr Pro Asp Phe Gln Leu
            130                 135                 140

Leu Asn Phe Ser Leu Pro Glu Glu Asp Thr Lys Leu Lys Ile Pro Leu
145                 150                 155                 160

Ile His Arg Ala Leu Gln Leu Ala Gln Arg Pro Val Ser Leu Leu Ala
            165                 170                 175

Ser Pro Trp Thr Ser Pro Thr Trp Leu Lys Thr Asn Gly Ala Val Asn
            180                 185                 190

Gly Lys Gly Ser Leu Lys Gly Gln Pro Gly Asp Ile Tyr His Gln Thr
            195                 200                 205

Trp Ala Arg Tyr Phe Val Lys Phe Leu Asp Ala Tyr Ala Glu His Lys
            210                 215                 220

Leu Gln Phe Trp Ala Val Thr Ala Glu Asn Glu Pro Ser Ala Gly Leu
225                 230                 235                 240

Leu Ser Gly Tyr Pro Phe Gln Cys Leu Gly Phe Thr Pro Glu His Gln
            245                 250                 255

Arg Asp Phe Ile Ala Arg Asp Leu Gly Pro Thr Leu Ala Asn Ser Thr
            260                 265                 270

His His Asn Val Arg Leu Leu Met Leu Asp Asp Gln Arg Leu Leu Leu
            275                 280                 285

Pro His Trp Ala Lys Val Val Leu Thr Asp Pro Glu Ala Ala Lys Tyr
            290                 295                 300

Val His Gly Ile Ala Val His Trp Tyr Leu Asp Phe Leu Ala Pro Ala
305                 310                 315                 320

Asn Ala Thr Leu Gly Glu Thr His Arg Leu Phe Pro Asn Thr Met Leu
            325                 330                 335

Phe Ala Ser Glu Ala Cys Val Gly Ser Lys Phe Trp Glu Gln Ser Val
            340                 345                 350

Arg Leu Gly Ser Trp Asp Arg Gly Met Gln Tyr Ser His Ser Ile Ile
            355                 360                 365

Thr Asn Leu Leu Tyr His Val Gly Trp Thr Asp Trp Asn Leu Ala
            370                 375                 380

Leu Asn Pro Glu Gly Gly Pro Asn Trp Val Arg Asn Phe Val Asp Ser
385                 390                 395                 400

Pro Ile Ile Val Asp Ile Thr Lys Asp Thr Phe Tyr Lys Gln Pro Met
            405                 410                 415

Phe Tyr His Leu Gly His Phe Ser Lys Phe Ile Pro Glu Gly Ser Gln
            420                 425                 430

Arg Val Gly Leu Val Ala Ser Gln Lys Asn Asp Leu Asp Ala Val Ala
            435                 440                 445

Leu Met His Pro Asp Gly Ser Ala Val Val Val Leu Asn Arg Ser
            450                 455                 460

Ser Lys Asp Val Pro Leu Thr Ile Lys Asp Pro Ala Val Gly Phe Leu
465                 470                 475                 480

Glu Thr Ile Ser Pro Gly Tyr Ser Ile His Thr Tyr Leu Trp Arg Arg
            485                 490                 495

Gln

<210> SEQ ID NO 10
<211> LENGTH: 497
<212> TYPE: PRT
<213> ORGANISM: Artificial Sequence
<220> FEATURE:
<223> OTHER INFORMATION: Human source organism, but with engineered mutation

<400> SEQUENCE: 10

| Ala | Arg | Pro | Cys | Ile | Pro | Lys | Ser | Phe | Gly | Tyr | Ser | Val | Val | Cys |
| 1 | | | | 5 | | | | | 10 | | | | | 15 |

| Val | Cys | Asn | Ala | Thr | Tyr | Cys | Asp | Ser | Phe | Asp | Pro | Pro | Thr | Phe | Pro |
| | | | 20 | | | | | 25 | | | | | 30 | | |

| Ala | Leu | Gly | Thr | Phe | Ser | Arg | Tyr | Glu | Ser | Thr | Arg | Ser | Gly | Arg | Arg |
| | | 35 | | | | | 40 | | | | | 45 | | | |

| Met | Glu | Leu | Ser | Met | Gly | Pro | Ile | Gln | Ala | Asn | His | Thr | Gly | Thr | Gly |
| | 50 | | | | | 55 | | | | | 60 | | | | |

| Leu | Leu | Leu | Thr | Leu | Gln | Pro | Glu | Gln | Lys | Phe | Gln | Lys | Val | Lys | Gly |
| 65 | | | | | 70 | | | | | 75 | | | | | 80 |

| Phe | Gly | Gly | Ala | Met | Thr | Asp | Ala | Ala | Ala | Leu | Asn | Ile | Leu | Ala | Leu |
| | | | | 85 | | | | | 90 | | | | | 95 | |

| Ser | Pro | Pro | Ala | Gln | Asn | Leu | Leu | Leu | Lys | Ser | Tyr | Phe | Ser | Glu | Glu |
| | | | 100 | | | | | 105 | | | | | 110 | | |

| Gly | Ile | Gly | Tyr | Asn | Ile | Ile | Arg | Val | Pro | Met | Ala | Ser | Cys | Asp | Phe |
| | | 115 | | | | | 120 | | | | | 125 | | | |

| Ser | Ile | Arg | Thr | Tyr | Thr | Tyr | Ala | Asp | Thr | Pro | Asp | Asp | Phe | Gln | Leu |
| | 130 | | | | | 135 | | | | | 140 | | | | |

| Leu | Asn | Phe | Ser | Leu | Pro | Glu | Glu | Asp | Thr | Lys | Leu | Lys | Ile | Pro | Leu |
| 145 | | | | | 150 | | | | | 155 | | | | | 160 |

| Ile | His | Arg | Ala | Leu | Gln | Leu | Ala | Gln | Arg | Pro | Val | Ser | Leu | Leu | Ala |
| | | | | 165 | | | | | 170 | | | | | 175 | |

| Ser | Pro | Trp | Thr | Ser | Pro | Thr | Trp | Leu | Lys | Thr | Asn | Gly | Ala | Val | Asn |
| | | | | 180 | | | | | 185 | | | | | 190 | |

| Gly | Lys | Gly | Ser | Leu | Lys | Gly | Gln | Pro | Gly | Asp | Ile | Tyr | His | Gln | Thr |
| | | 195 | | | | | 200 | | | | | 205 | | | |

| Trp | Ala | Arg | Tyr | Phe | Val | Lys | Phe | Leu | Asp | Ala | Tyr | Ala | Glu | His | Lys |
| | 210 | | | | | 215 | | | | | 220 | | | | |

| Leu | Gln | Phe | Trp | Ala | Val | Thr | Ala | Glu | Asn | Glu | Pro | Ser | Ala | Gly | Leu |
| 225 | | | | | 230 | | | | | 235 | | | | | 240 |

| Leu | Ser | Gly | Tyr | Pro | Phe | Gln | Cys | Leu | Gly | Phe | Thr | Pro | Glu | His | Gln |
| | | | | 245 | | | | | 250 | | | | | 255 | |

| Arg | Asp | Phe | Ile | Ala | Arg | Asp | Leu | Gly | Pro | Thr | Leu | Ala | Asn | Ser | Thr |
| | | | 260 | | | | | 265 | | | | | 270 | | |

| His | His | Asn | Val | Arg | Leu | Leu | Met | Leu | Asp | Asp | Gln | Arg | Leu | Leu | Leu |
| | | 275 | | | | | 280 | | | | | 285 | | | |

| Pro | His | Trp | Ala | Lys | Val | Val | Leu | Thr | Asp | Pro | Glu | Ala | Ala | Lys | Tyr |
| | 290 | | | | | 295 | | | | | 300 | | | | |

| Val | His | Gly | Ile | Ala | Val | His | Trp | Tyr | Leu | Asp | Ala | Phe | Ala | Pro | Ala |
| 305 | | | | | 310 | | | | | 315 | | | | | 320 |

| Asn | Ala | Thr | Leu | Gly | Glu | Thr | His | Arg | Leu | Phe | Pro | Asn | Thr | Met | Leu |
| | | | | 325 | | | | | 330 | | | | | 335 | |

| Phe | Ala | Ser | Glu | Ala | Cys | Val | Gly | Ser | Lys | Phe | Trp | Glu | Gln | Ser | Val |
| | | | 340 | | | | | 345 | | | | | 350 | | |

| Arg | Leu | Gly | Ser | Trp | Asp | Arg | Gly | Met | Gln | Tyr | Ser | His | Ser | Ile | Ile |
| | | 355 | | | | | 360 | | | | | 365 | | | |

| Thr | Asn | Leu | Leu | Tyr | His | Val | Val | Gly | Trp | Thr | Asp | Trp | Asn | Leu | Ala |
| | 370 | | | | | 375 | | | | | 380 | | | | |

| Leu | Asn | Pro | Glu | Gly | Gly | Pro | Asn | Trp | Val | Arg | Asn | Phe | Val | Asp | Ser |
| 385 | | | | | 390 | | | | | 395 | | | | | 400 |

```
Pro Ile Ile Val Asp Ile Thr Lys Asp Thr Phe Tyr Lys Gln Pro Met
                405                 410                 415
Phe Tyr His Leu Gly His Phe Ser Lys Phe Ile Pro Glu Gly Ser Gln
            420                 425                 430
Arg Val Gly Leu Val Ala Ser Gln Lys Asn Asp Leu Asp Ala Val Ala
        435                 440                 445
Leu Met His Pro Asp Gly Ser Ala Val Val Val Leu Asn Arg Ser
450                 455                 460
Ser Lys Asp Val Pro Leu Thr Ile Lys Asp Pro Ala Val Gly Phe Leu
465                 470                 475                 480
Glu Thr Ile Ser Pro Gly Tyr Ser Ile His Thr Tyr Leu Trp Arg Arg
                485                 490                 495
Gln

<210> SEQ ID NO 11
<211> LENGTH: 497
<212> TYPE: PRT
<213> ORGANISM: Artificial Sequence
<220> FEATURE:
<223> OTHER INFORMATION: Human source organism, but with engineered
      mutation

<400> SEQUENCE: 11

Ala Arg Pro Cys Ile Pro Lys Ser Phe Gly Tyr Ser Ser Val Val Cys
1               5                   10                  15
Val Cys Asn Ala Thr Tyr Cys Asp Ser Phe Asp Pro Pro Thr Phe Pro
            20                  25                  30
Ala Leu Gly Thr Phe Ser Arg Tyr Glu Ser Thr Arg Ser Gly Arg Arg
        35                  40                  45
Met Glu Leu Ser Met Gly Pro Ile Gln Ala Asn His Thr Gly Thr Gly
    50                  55                  60
Leu Leu Leu Thr Leu Gln Pro Glu Gln Lys Phe Gln Lys Val Lys Gly
65                  70                  75                  80
Phe Gly Gly Ala Met Thr Asp Ala Ala Ala Leu Asn Ile Leu Ala Leu
                85                  90                  95
Ser Pro Pro Ala Gln Asn Leu Leu Leu Lys Ser Tyr Phe Ser Glu Glu
            100                 105                 110
Gly Ile Gly Tyr Asn Ile Ile Arg Val Pro Met Ala Ser Cys Asp Phe
        115                 120                 125
Ser Ile Arg Thr Tyr Thr Tyr Ala Asp Thr Pro Asp Asp Phe Gln Leu
    130                 135                 140
His Asn Phe Ser Leu Pro Glu Glu Asp Thr Lys Leu Lys Ile Pro Leu
145                 150                 155                 160
Ile His Arg Ala Leu Gln Leu Ala Gln Arg Pro Val Ser Leu Leu Ala
                165                 170                 175
Ser Pro Trp Thr Ser Pro Thr Trp Leu Lys Thr Asn Gly Ala Val Asn
            180                 185                 190
Gly Lys Gly Ser Leu Lys Gly Gln Pro Gly Asp Ile Tyr His Gln Thr
        195                 200                 205
Trp Ala Arg Tyr Phe Val Lys Phe Leu Asp Ala Tyr Ala Glu His Lys
    210                 215                 220
Leu Gln Phe Trp Ala Val Thr Ala Glu Asn Glu Pro Ser Ala Gly Leu
225                 230                 235                 240
Leu Ser Gly Tyr Pro Phe Gln Cys Leu Gly Phe Thr Pro Glu His Gln
                245                 250                 255
```

```
Arg Asp Phe Ile Ala Arg Asp Leu Gly Pro Thr Leu Ala Asn Ser Thr
                260                 265                 270

His His Asn Val Arg Leu Leu Met Leu Asp Asp Gln Arg Leu Leu Leu
        275                 280                 285

Pro His Trp Ala Lys Val Val Leu Thr Asp Pro Glu Ala Ala Lys Tyr
    290                 295                 300

Val His Gly Ile Ala Val His Trp Tyr Leu Asp Phe Leu Ala Pro Ala
305                 310                 315                 320

Ala Ala Thr Leu Gly Glu Thr His Arg Leu Phe Pro Asn Thr Met Leu
                325                 330                 335

Phe Ala Ser Glu Ala Cys Val Gly Ser Lys Phe Trp Glu Gln Ser Val
        340                 345                 350

Arg Leu Gly Ser Trp Asp Arg Gly Met Gln Tyr Ser His Ser Ile Ile
    355                 360                 365

Thr Asn Leu Leu Tyr His Val Gly Trp Thr Asp Trp Asn Leu Ala
370                 375                 380

Leu Asn Pro Glu Gly Gly Pro Asn Trp Val Arg Asn Phe Val Asp Ser
385                 390                 395                 400

Pro Ile Ile Val Asp Ile Thr Lys Asp Thr Phe Tyr Lys Gln Pro Met
            405                 410                 415

Phe Tyr His Leu Gly His Phe Ser Lys Phe Ile Pro Glu Gly Ser Gln
        420                 425                 430

Arg Val Gly Leu Val Ala Ser Gln Lys Asn Asp Leu Asp Ala Val Ala
    435                 440                 445

Leu Met His Pro Asp Gly Ser Ala Val Val Val Leu Asn Arg Ser
450                 455                 460

Ser Lys Asp Val Pro Leu Thr Ile Lys Asp Pro Ala Val Gly Phe Leu
465                 470                 475                 480

Glu Thr Ile Ser Pro Gly Tyr Ser Ile His Thr Tyr Leu Trp Arg Arg
                485                 490                 495

Gln

<210> SEQ ID NO 12
<211> LENGTH: 497
<212> TYPE: PRT
<213> ORGANISM: Artificial Sequence
<220> FEATURE:
<223> OTHER INFORMATION: Human source organism, but with engineered
      mutation

<400> SEQUENCE: 12

Ala Arg Pro Cys Ile Pro Lys Ser Phe Gly Tyr Ser Ser Val Val Cys
1               5                   10                  15

Val Cys Asn Ala Thr Tyr Cys Asp Ser Phe Asp Pro Pro Thr Phe Pro
            20                  25                  30

Ala Leu Gly Thr Phe Ser Arg Tyr Glu Ser Thr Arg Ser Gly Arg Arg
        35                  40                  45

Met Glu Leu Ser Met Gly Pro Ile Gln Ala Asn His Thr Gly Thr Gly
    50                  55                  60

Leu Leu Leu Thr Leu Gln Pro Glu Gln Lys Phe Gln Lys Val Lys Gly
65                  70                  75                  80

Phe Gly Gly Ala Met Thr Asp Ala Ala Ala Leu Asn Ile Leu Ala Leu
                85                  90                  95

Ser Pro Pro Ala Gln Asn Leu Leu Leu Lys Ser Tyr Phe Ser Glu Glu
            100                 105                 110
```

```
Gly Ile Gly Tyr Asn Ile Ile Arg Val Pro Met Ala Ser Cys Asp Phe
            115                 120                 125

Ser Ile Arg Thr Tyr Thr Tyr Ala Asp Thr Pro Asp Asp Phe Gln Leu
130                 135                 140

His Asn Phe Ser Leu Pro Glu Glu Asp Thr Lys Leu Lys Ile Pro Leu
145                 150                 155                 160

Ile His Arg Ala Leu Gln Leu Ala Gln Arg Pro Val Ser Leu Leu Ala
                165                 170                 175

Ser Pro Trp Thr Ser Pro Thr Trp Leu Lys Thr Asn Gly Ala Val Asn
            180                 185                 190

Gly Lys Gly Ser Leu Lys Gly Gln Pro Gly Asp Ile Tyr His Gln Thr
        195                 200                 205

Trp Ala Arg Tyr Phe Val Lys Phe Leu Asp Ala Tyr Ala Glu His Lys
210                 215                 220

Leu Gln Phe Trp Ala Val Thr Ala Glu Asn Glu Pro Ser Ala Gly Leu
225                 230                 235                 240

Leu Ser Gly Tyr Pro Phe Gln Cys Leu Gly Phe Thr Pro Glu His Gln
                245                 250                 255

Arg Asp Phe Ile Ala Arg Asp Leu Gly Pro Thr Leu Ala Asn Ser Thr
            260                 265                 270

His His Asn Val Arg Leu Leu Met Leu Asp Asp Gln Arg Leu Leu Leu
        275                 280                 285

Pro His Trp Ala Lys Val Val Leu Thr Asp Pro Glu Ala Ala Lys Tyr
290                 295                 300

Val His Gly Ile Ala Val His Trp Tyr Leu Asp Phe Leu Ala Pro Ala
305                 310                 315                 320

Val Ala Thr Leu Gly Glu Thr His Arg Leu Phe Pro Asn Thr Met Leu
                325                 330                 335

Phe Ala Ser Glu Ala Cys Val Gly Ser Lys Phe Trp Glu Gln Ser Val
            340                 345                 350

Arg Leu Gly Ser Trp Asp Arg Gly Met Gln Tyr Ser His Ser Ile Ile
        355                 360                 365

Thr Asn Leu Leu Tyr His Val Val Gly Trp Thr Asp Trp Asn Leu Ala
370                 375                 380

Leu Asn Pro Glu Gly Gly Pro Asn Trp Val Arg Asn Phe Val Asp Ser
385                 390                 395                 400

Pro Ile Ile Val Asp Ile Thr Lys Asp Thr Phe Tyr Lys Gln Pro Met
                405                 410                 415

Phe Tyr His Leu Gly His Phe Ser Lys Phe Ile Pro Glu Gly Ser Gln
            420                 425                 430

Arg Val Gly Leu Val Ala Ser Gln Lys Asn Asp Leu Asp Ala Val Ala
        435                 440                 445

Leu Met His Pro Asp Gly Ser Ala Val Val Val Leu Asn Arg Ser
450                 455                 460

Ser Lys Asp Val Pro Leu Thr Ile Lys Asp Pro Ala Val Gly Phe Leu
465                 470                 475                 480

Glu Thr Ile Ser Pro Gly Tyr Ser Ile His Thr Tyr Leu Trp Arg Arg
                485                 490                 495

Gln

<210> SEQ ID NO 13
<211> LENGTH: 497
<212> TYPE: PRT
<213> ORGANISM: Artificial Sequence
```

<220> FEATURE:
<223> OTHER INFORMATION: Human source organism, but with engineered
     mutation

<400> SEQUENCE:

```
385                 390                 395                 400
Pro Ile Ile Val Asp Ile Thr Lys Asp Thr Phe Tyr Lys Gln Pro Met
                405                 410                 415

Phe Tyr His Leu Gly His Phe Ser Lys Phe Ile Pro Glu Gly Ser Gln
                420                 425                 430

Arg Val Gly Leu Val Ala Ser Gln Lys Asn Asp Leu Asp Ala Val Ala
                435                 440                 445

Leu Met His Pro Asp Gly Ser Ala Val Val Val Leu Asn Arg Ser
                450                 455                 460

Ser Lys Asp Val Pro Leu Thr Ile Lys Asp Pro Ala Val Gly Phe Leu
465                 470                 475                 480

Glu Thr Ile Ser Pro Gly Tyr Ser Ile His Thr Tyr Leu Trp Arg Arg
                485                 490                 495

Gln

<210> SEQ ID NO 14
<211> LENGTH: 497
<212> TYPE: PRT
<213> ORGANISM: Artificial Sequence
<220> FEATURE:
<223> OTHER INFORMATION: Human source organism, but with engineered
      mutation

<400> SEQUENCE: 14

Ala Arg Pro Cys Ile Pro Lys Ser Phe Gly Tyr Ser Ser Val Val Cys
1               5                   10                  15

Val Cys Asn Ala Thr Tyr Cys Asp Ser Phe Asp Pro Pro Thr Phe Pro
                20                  25                  30

Ala Leu Gly Thr Phe Ser Arg Tyr Glu Ser Thr Arg Ser Gly Arg Arg
                35                  40                  45

Met Glu Leu Ser Met Gly Pro Ile Gln Ala Asn His Thr Gly Thr Gly
            50                  55                  60

Leu Leu Leu Thr Leu Gln Pro Glu Gln Lys Phe Gln Lys Val Lys Gly
65                  70                  75                  80

Phe Gly Gly Ala Met Thr Asp Ala Ala Ala Leu Asn Ile Leu Ala Leu
                85                  90                  95

Ser Pro Pro Ala Gln Asn Leu Leu Leu Lys Ser Tyr Phe Ser Glu Glu
                100                 105                 110

Gly Ile Gly Tyr Asn Ile Ile Arg Val Pro Met Ala Ser Cys Asp Phe
                115                 120                 125

Ser Ile Arg Thr Tyr Thr Tyr Ala Asp Thr Pro Asp Asp Phe Gln Leu
                130                 135                 140

His Asn Phe Ser Leu Pro Glu Glu Asp Thr Lys Leu Lys Ile Pro Leu
145                 150                 155                 160

Ile His Arg Ala Leu Gln Leu Ala Gln Arg Pro Val Ser Leu Leu Ala
                165                 170                 175

Ser Pro Trp Thr Ser Pro Thr Trp Leu Lys Thr Asn Gly Ala Val Asn
                180                 185                 190

Gly Lys Gly Ser Leu Lys Gly Gln Pro Gly Asp Ile Tyr His Gln Thr
                195                 200                 205

Trp Ala Arg Tyr Phe Val Lys Phe Leu Asp Ala Tyr Ala Glu His Lys
                210                 215                 220

Leu Gln Phe Trp Ala Val Thr Ala Glu Asn Glu Pro Ser Ala Gly Leu
225                 230                 235                 240

Leu Ser Gly Tyr Pro Phe Gln Cys Leu Gly Phe Thr Pro Glu His Gln
```

245                 250                 255
Arg Asp Phe Ile Ala Arg Asp Leu Gly Pro Thr Leu Ala Asn Ser Thr
                260                 265                 270

His His Asn Val Arg Leu Leu Met Leu Asp Asp Gln Arg Leu Leu Leu
            275                 280                 285

Pro His Trp Ala Lys Val Val Leu Thr Asp Pro Glu Ala Ala Lys Tyr
        290                 295                 300

Val His Gly Ile Ala Val His Trp Tyr Leu Asp Ala Phe Ala Pro Ala
305                 310                 315                 320

Val Ala Thr Leu Gly Glu Thr His Arg Leu Phe Pro Asn Thr Met Leu
                325                 330                 335

Phe Ala Ser Glu Ala Cys Val Gly Ser Lys Phe Trp Glu Gln Ser Val
            340                 345                 350

Arg Leu Gly Ser Trp Asp Arg Gly Met Gln Tyr Ser His Ser Ile Ile
        355                 360                 365

Thr Asn Leu Leu Tyr His Val Val Gly Trp Thr Asp Trp Asn Leu Ala
370                 375                 380

Leu Asn Pro Glu Gly Gly Pro Asn Trp Val Arg Asn Phe Val Asp Ser
385                 390                 395                 400

Pro Ile Ile Val Asp Ile Thr Lys Asp Thr Phe Tyr Lys Gln Pro Met
                405                 410                 415

Phe Tyr His Leu Gly His Phe Ser Lys Phe Ile Pro Glu Gly Ser Gln
            420                 425                 430

Arg Val Gly Leu Val Ala Ser Gln Lys Asn Asp Leu Asp Ala Val Ala
        435                 440                 445

Leu Met His Pro Asp Gly Ser Ala Val Val Val Leu Asn Arg Ser Ser
450                 455                 460

Ser Lys Asp Val Pro Leu Thr Ile Lys Asp Pro Ala Val Gly Phe Leu
465                 470                 475                 480

Glu Thr Ile Ser Pro Gly Tyr Ser Ile His Thr Tyr Leu Trp Arg Arg
                485                 490                 495

Gln

<210> SEQ ID NO 15
<211> LENGTH: 497
<212> TYPE: PRT
<213> ORGANISM: Artificial Sequence
<220> FEATURE:
<223> OTHER INFORMATION: Human source organism, but with engineered
      mutation

<400> SEQUENCE: 15

Ala Arg Pro Cys Ile Pro Lys Ser Phe Gly Tyr Ser Ser Val Val Cys
1               5                   10                  15

Val Cys Asn Ala Thr Tyr Cys Asp Ser Phe Asp Pro Thr Phe Pro
            20                  25                  30

Ala Leu Gly Thr Phe Ser Arg Tyr Glu Ser Thr Arg Ser Gly Arg Arg
        35                  40                  45

Met Glu Leu Ser Met Gly Pro Ile Gln Ala Asn His Thr Gly Thr Gly
    50                  55                  60

Leu Leu Leu Thr Leu Gln Pro Glu Gln Lys Phe Gln Lys Val Lys Gly
65                  70                  75                  80

Phe Gly Gly Ala Met Thr Asp Ala Ala Ala Leu Asn Ile Leu Ala Leu
                85                  90                  95

Ser Pro Pro Ala Gln Asn Leu Leu Leu Lys Ser Tyr Phe Ser Glu Glu

```
            100                 105                 110
Gly Ile Gly Tyr Asn Ile Ile Arg Val Pro Met Ala Ser Cys Asp Phe
        115                 120                 125

Ser Ile Arg Thr Tyr Thr Tyr Ala Asp Thr Pro Asp Asp Phe Gln Leu
130                 135                 140

Leu Asn Phe Ser Leu Pro Glu Glu Asp Thr Lys Leu Lys Ile Pro Leu
145                 150                 155                 160

Ile His Arg Ala Leu Gln Leu Ala Gln Arg Pro Val Ser Leu Leu Ala
                165                 170                 175

Ser Pro Trp Thr Ser Pro Thr Trp Leu Lys Thr Asn Gly Ala Val Asn
            180                 185                 190

Gly Lys Gly Ser Leu Lys Gly Gln Pro Gly Asp Ile Tyr His Gln Thr
        195                 200                 205

Trp Ala Arg Tyr Phe Val Lys Phe Leu Asp Ala Tyr Ala Glu His Lys
    210                 215                 220

Leu Gln Phe Trp Ala Val Thr Ala Glu Asn Glu Pro Ser Ala Gly Leu
225                 230                 235                 240

Leu Ser Gly Tyr Pro Phe Gln Cys Leu Gly Phe Thr Pro Glu His Gln
                245                 250                 255

Arg Asp Phe Ile Ala Arg Asp Leu Gly Pro Thr Leu Ala Asn Ser Thr
            260                 265                 270

His His Asn Val Arg Leu Leu Met Leu Asp Asp Gln Arg Leu Leu Leu
        275                 280                 285

Pro His Trp Ala Lys Val Val Leu Thr Asp Pro Glu Ala Ala Lys Tyr
    290                 295                 300

Val His Gly Ile Ala Val His Trp Tyr Leu Asp Phe Leu Ala Pro Ala
305                 310                 315                 320

Ala Ala Thr Leu Gly Glu Thr His Arg Leu Phe Pro Asn Thr Met Leu
                325                 330                 335

Phe Ala Ser Glu Ala Cys Val Gly Ser Lys Phe Trp Glu Gln Ser Val
            340                 345                 350

Arg Leu Gly Ser Trp Asp Arg Gly Met Gln Tyr Ser His Ser Ile Ile
        355                 360                 365

Thr Asn Leu Leu Tyr His Val Val Gly Trp Thr Asp Trp Asn Leu Ala
    370                 375                 380

Leu Asn Pro Glu Gly Gly Pro Asn Trp Val Arg Asn Phe Val Asp Ser
385                 390                 395                 400

Pro Ile Ile Val Asp Ile Thr Lys Asp Thr Phe Tyr Lys Gln Pro Met
                405                 410                 415

Phe Tyr His Leu Gly His Phe Ser Lys Phe Ile Pro Glu Gly Ser Gln
            420                 425                 430

Arg Val Gly Leu Val Ala Ser Gln Lys Asn Asp Leu Asp Ala Val Ala
        435                 440                 445

Leu Met His Pro Asp Gly Ser Ala Val Val Val Leu Asn Arg Ser
    450                 455                 460

Ser Lys Asp Val Pro Leu Thr Ile Lys Asp Pro Ala Val Gly Phe Leu
465                 470                 475                 480

Glu Thr Ile Ser Pro Gly Tyr Ser Ile His Thr Tyr Leu Trp Arg Arg
                485                 490                 495

Gln

<210> SEQ ID NO 16
<211> LENGTH: 497
```

<212> TYPE: PRT
<213> ORGANISM: Artificial Sequence
<220> FEATURE:
<223> OTHER INFORMATION: Human source organism, but with engineered mutation

<400> SEQUENCE: 16

```
Ala Arg Pro Cys Ile Pro Lys Ser Phe Gly Tyr Ser Ser Val Val Cys
1               5                   10                  15

Val Cys Asn Ala Thr Tyr Cys Asp Ser Phe Asp Pro Pro Thr Phe Pro
            20                  25                  30

Ala Leu Gly Thr Phe Ser Arg Tyr Glu Ser Thr Arg Ser Gly Arg Arg
        35                  40                  45

Met Glu Leu Ser Met Gly Pro Ile Gln Ala Asn His Thr Gly Thr Gly
    50                  55                  60

Leu Leu Leu Thr Leu Gln Pro Glu Gln Lys Phe Gln Lys Val Lys Gly
65                  70                  75                  80

Phe Gly Gly Ala Met Thr Asp Ala Ala Ala Leu Asn Ile Leu Ala Leu
                85                  90                  95

Ser Pro Pro Ala Gln Asn Leu Leu Leu Lys Ser Tyr Phe Ser Glu Glu
            100                 105                 110

Gly Ile Gly Tyr Asn Ile Ile Arg Val Pro Met Ala Ser Cys Asp Phe
        115                 120                 125

Ser Ile Arg Thr Tyr Thr Tyr Ala Asp Thr Pro Asp Asp Phe Gln Leu
    130                 135                 140

Leu Asn Phe Ser Leu Pro Glu Glu Asp Thr Lys Leu Lys Ile Pro Leu
145                 150                 155                 160

Ile His Arg Ala Leu Gln Leu Ala Gln Arg Pro Val Ser Leu Leu Ala
                165                 170                 175

Ser Pro Trp Thr Ser Pro Thr Trp Leu Lys Thr Asn Gly Ala Val Asn
            180                 185                 190

Gly Lys Gly Ser Leu Lys Gly Gln Pro Gly Asp Ile Tyr His Gln Thr
        195                 200                 205

Trp Ala Arg Tyr Phe Val Lys Phe Leu Asp Ala Tyr Ala Glu His Lys
    210                 215                 220

Leu Gln Phe Trp Ala Val Thr Ala Glu Asn Glu Pro Ser Ala Gly Leu
225                 230                 235                 240

Leu Ser Gly Tyr Pro Phe Gln Cys Leu Gly Phe Thr Pro Glu His Gln
                245                 250                 255

Arg Asp Phe Ile Ala Arg Asp Leu Gly Pro Thr Leu Ala Asn Ser Thr
            260                 265                 270

His His Asn Val Arg Leu Leu Met Leu Asp Asp Gln Arg Leu Leu Leu
        275                 280                 285

Pro His Trp Ala Lys Val Val Leu Thr Asp Pro Glu Ala Ala Lys Tyr
    290                 295                 300

Val His Gly Ile Ala Val His Trp Tyr Leu Asp Phe Leu Ala Pro Ala
305                 310                 315                 320

Val Ala Thr Leu Gly Glu Thr His Arg Leu Phe Pro Asn Thr Met Leu
                325                 330                 335

Phe Ala Ser Glu Ala Cys Val Gly Ser Lys Phe Trp Glu Gln Ser Val
            340                 345                 350

Arg Leu Gly Ser Trp Asp Arg Gly Met Gln Tyr Ser His Ser Ile Ile
        355                 360                 365

Thr Asn Leu Leu Tyr His Val Val Gly Trp Thr Asp Trp Asn Leu Ala
    370                 375                 380
```

```
Leu Asn Pro Glu Gly Gly Pro Asn Trp Val Arg Asn Phe Val Asp Ser
385                 390                 395                 400

Pro Ile Ile Val Asp Ile Thr Lys Asp Thr Phe Tyr Lys Gln Pro Met
                405                 410                 415

Phe Tyr His Leu Gly His Phe Ser Lys Phe Ile Pro Glu Gly Ser Gln
            420                 425                 430

Arg Val Gly Leu Val Ala Ser Gln Lys Asn Asp Leu Asp Ala Val Ala
        435                 440                 445

Leu Met His Pro Asp Gly Ser Ala Val Val Val Leu Asn Arg Ser
    450                 455                 460

Ser Lys Asp Val Pro Leu Thr Ile Lys Asp Pro Ala Val Gly Phe Leu
465                 470                 475                 480

Glu Thr Ile Ser Pro Gly Tyr Ser Ile His Thr Tyr Leu Trp Arg Arg
                485                 490                 495

Gln

<210> SEQ ID NO 17
<211> LENGTH: 15
<212> TYPE: PRT
<213> ORGANISM: Homo sapiens

<400> SEQUENCE: 17

Asp Asp Phe Gln Leu His Asn Phe Ser Leu Pro Glu Glu Asp Thr
1               5                   10                  15

<210> SEQ ID NO 18
<211> LENGTH: 15
<212> TYPE: PRT
<213> ORGANISM: S. scorfa

<400> SEQUENCE: 18

Asp Asp Phe Gln Leu Leu Asn Phe Ser Leu Pro Glu Glu Asp Val
1               5                   10                  15

<210> SEQ ID NO 19
<211> LENGTH: 15
<212> TYPE: PRT
<213> ORGANISM: B. taurus

<400> SEQUENCE: 19

Asp Asp Phe Gln Leu Leu Asn Phe Ser Leu Pro Glu Glu Asp Val
1               5                   10                  15

<210> SEQ ID NO 20
<211> LENGTH: 15
<212> TYPE: PRT
<213> ORGANISM: Murine sp.

<400> SEQUENCE: 20

Asn Asp Phe Gln Leu Ser Asn Phe Ser Leu Pro Glu Glu Asp Thr
1               5                   10                  15

<210> SEQ ID NO 21
<211> LENGTH: 13
<212> TYPE: PRT
<213> ORGANISM: Homo sapiens

<400> SEQUENCE: 21

Asp Phe Leu Ala Pro Ala Lys Ala Thr Leu Gly Glu Thr
1               5                   10
```

<210> SEQ ID NO 22
<211> LENGTH: 13
<212> TYPE: PRT
<213> ORGANISM: S. scorfa

<400> SEQUENCE: 22

Asp Phe Leu Ala Pro Ala Lys Ala Thr Leu Gly Glu Thr
1               5                   10

<210> SEQ ID NO 23
<211> LENGTH: 13
<212> TYPE: PRT
<213> ORGANISM: B. taurus

<400> SEQUENCE: 23

Asp Phe Leu Ala Pro Ala Asn Ala Thr Leu Gly Glu Thr
1               5                   10

<210> SEQ ID NO 24
<211> LENGTH: 13
<212> TYPE: PRT
<213> ORGANISM: Murine sp.

<400> SEQUENCE: 24

Asp Phe Leu Ala Pro Ala Lys Ala Thr Leu Gly Glu Thr
1               5                   10

<210> SEQ ID NO 25
<211> LENGTH: 44
<212> TYPE: DNA
<213> ORGANISM: Artificial Sequence
<220> FEATURE:
<223> OTHER INFORMATION: Synthetic primer

<400> SEQUENCE: 25
ggcaagatct gaattcggga tggagttttc aagtccttcc agag            44

<210> SEQ ID NO 26
<211> LENGTH: 45
<212> TYPE: DNA
<213> ORGANISM: Artificial Sequence
<220> FEATURE:
<223> OTHER INFORMATION: Synthetic primer

<400> SEQUENCE: 26
tcgagcggcc gcaagctagc ttatcactgg cgacgccaca ggtag           45

<210> SEQ ID NO 27
<211> LENGTH: 20
<212> TYPE: DNA
<213> ORGANISM: Artificial Sequence
<220> FEATURE:
<223> OTHER INFORMATION: Synthetic primer

<400> SEQUENCE: 27
tccagccaac gccaccctag                                       20

<210> SEQ ID NO 28
<211> LENGTH: 20
<212> TYPE: DNA
<213> ORGANISM: Artificial Sequence
<220> FEATURE:
<223> OTHER INFORMATION: Synthetic primer

<400> SEQUENCE: 28
ctagggtggc gttggctgga                                        20

<210> SEQ ID NO 29
<211> LENGTH: 28
<212> TYPE: DNA
<213> ORGANISM: Artificial Sequence
<220> FEATURE:
<223> OTHER INFORMATION: Synthetic primer

<400> SEQUENCE: 29
tgatttccag ttgttgaact tcagcctc                               28

<210> SEQ ID NO 30
<211> LENGTH: 28
<212> TYPE: DNA
<213> ORGANISM: Artificial Sequence
<220> FEATURE:
<223> OTHER INFORMATION: Synthetic primer

<400> SEQUENCE: 30
gaggctgaag ttcaacaact ggaaatca                               28

<210> SEQ ID NO 31
<211> LENGTH: 28
<212> TYPE: DNA
<213> ORGANISM: Artificial Sequence
<220> FEATURE:
<223> OTHER INFORMATION: Synthetic primer

<400> SEQUENCE: 31
tgatttccag ttgttcaact tcagcctc                               28

<210> SEQ ID NO 32
<211> LENGTH: 28
<212> TYPE: DNA
<213> ORGANISM: Artificial Sequence
<220> FEATURE:
<223> OTHER INFORMATION: Synthetic primer

<400> SEQUENCE: 32
gaggctgaag ttgaacaact ggaaatca                               28

<210> SEQ ID NO 33
<211> LENGTH: 20
<212> TYPE: DNA
<213> ORGANISM: Artificial Sequence
<220> FEATURE:
<223> OTHER INFORMATION: Synthetic primer

<400> SEQUENCE: 33
tccagccgca gccaccctag                                        20

<210> SEQ ID NO 34
<211> LENGTH: 19
<212> TYPE: DNA
<213> ORGANISM: Artificial Sequence
<220> FEATURE:
<223> OTHER INFORMATION: Synthetic primer

<400> SEQUENCE: 34
ctagggtggt gcggctgga                                         19

<210> SEQ ID NO 35
<211> LENGTH: 21
<212> TYPE: DNA
<213> ORGANISM: Artificial Sequence

```
<220> FEATURE:
<223> OTHER INFORMATION: Synthetic primer

<400> SEQUENCE: 35
tccagccgta gccaccctag g                                          21

<210> SEQ ID NO 36
<211> LENGTH: 21
<212> TYPE: DNA
<213> ORGANISM: Artificial Sequence
<220> FEATURE:
<223> OTHER INFORMATION: Synthetic primer

<400> SEQUENCE: 36
cctagggtgg ctacggctgg a                                          21
```